United States Patent
Bomar et al.

(10) Patent No.: US 10,932,795 B2
(45) Date of Patent: Mar. 2, 2021

(54) CUTTING GUIDE AND METHOD

(71) Applicant: Smith & Nephew, Inc., Memphis, TN (US)

(72) Inventors: Bradley Bomar, Memphis, TN (US); Jeffrey Yeager, Nesbit, MS (US); Haixiang Hu, Collierville, TN (US); Jason Jordan, Hernando, MS (US); Christopher Cyko, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 16/642,141

(22) PCT Filed: Aug. 30, 2018

(86) PCT No.: PCT/US2018/048727
§ 371 (c)(1),
(2) Date: Feb. 26, 2020

(87) PCT Pub. No.: WO2019/046518
PCT Pub. Date: Mar. 7, 2019

(65) Prior Publication Data
US 2020/0297353 A1 Sep. 24, 2020

Related U.S. Application Data

(60) Provisional application No. 62/635,383, filed on Feb. 26, 2018, provisional application No. 62/552,978, filed on Aug. 31, 2017.

(51) Int. Cl.
| | | |
|---|---|---|
| A61B 17/58 | (2006.01) | |
| A61B 17/60 | (2006.01) | |
| A61F 2/00 | (2006.01) | |
| A61B 17/15 | (2006.01) | |
| A61B 17/00 | (2006.01) | |

(52) U.S. Cl.
CPC .. *A61B 17/157* (2013.01); *A61B 2017/00477* (2013.01)

(58) Field of Classification Search
CPC combination set(s) only.
See application file for complete search history.

(56) References Cited

U.S. PATENT DOCUMENTS

| | | |
|---|---|---|
| 5,197,944 A | 3/1993 | Steele |
| 2005/0187557 A1* | 8/2005 | Collazo ............... A61B 17/157 606/87 |
| 2014/0094815 A1 | 4/2014 | Kecman et al. |
| 2014/0324054 A1 | 10/2014 | Dmuschewsky |

\* cited by examiner

*Primary Examiner* — Sameh R Boles
(74) *Attorney, Agent, or Firm* — David Chambers

(57) ABSTRACT

Embodiments of the invention include a cutting guide (360) and methods of using the cutting guide to prepare bone for one or more knee arthroplasty implants. Some embodiments include an alignment mechanism (200), a cutting head (300), and an ankle clamp (400).

31 Claims, 26 Drawing Sheets

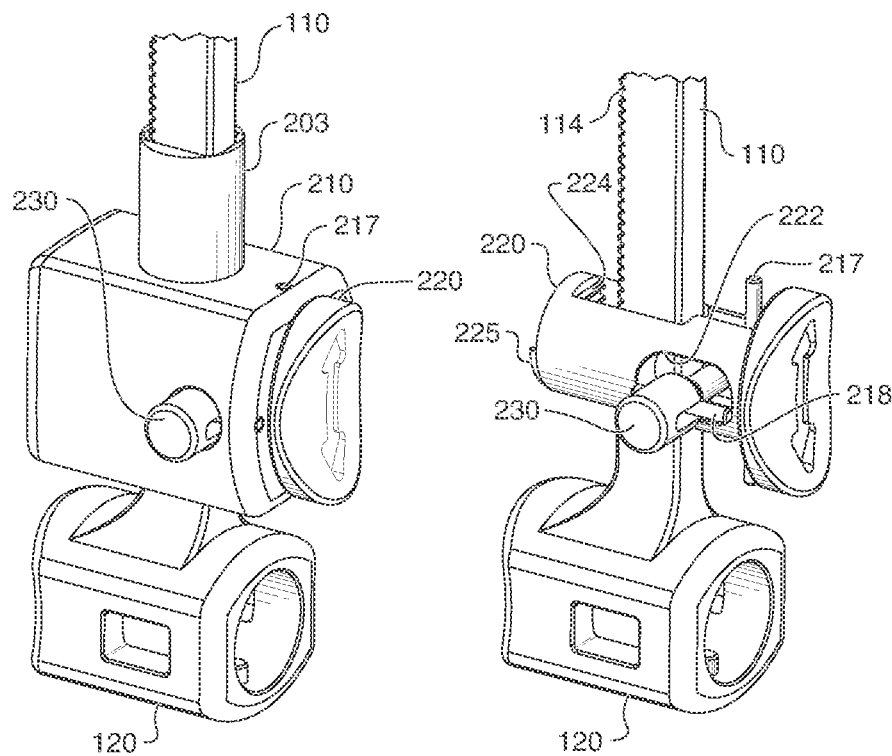
FIG. 6
FIG. 7
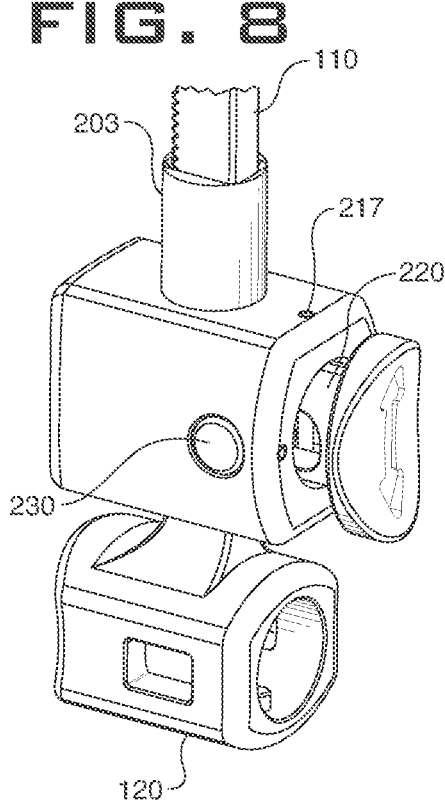
FIG. 8
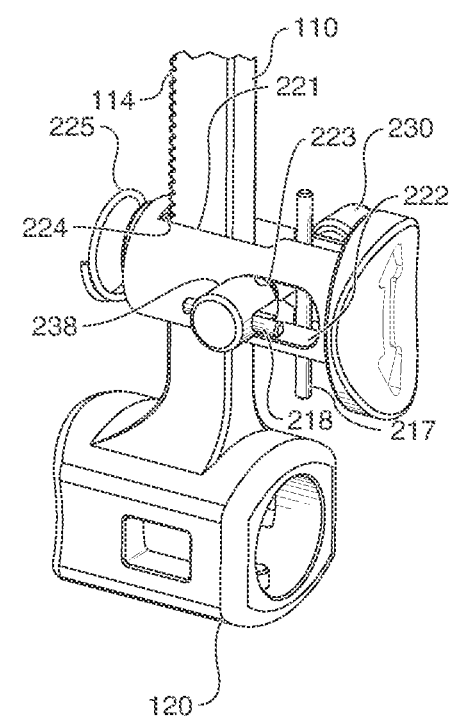
FIG. 9

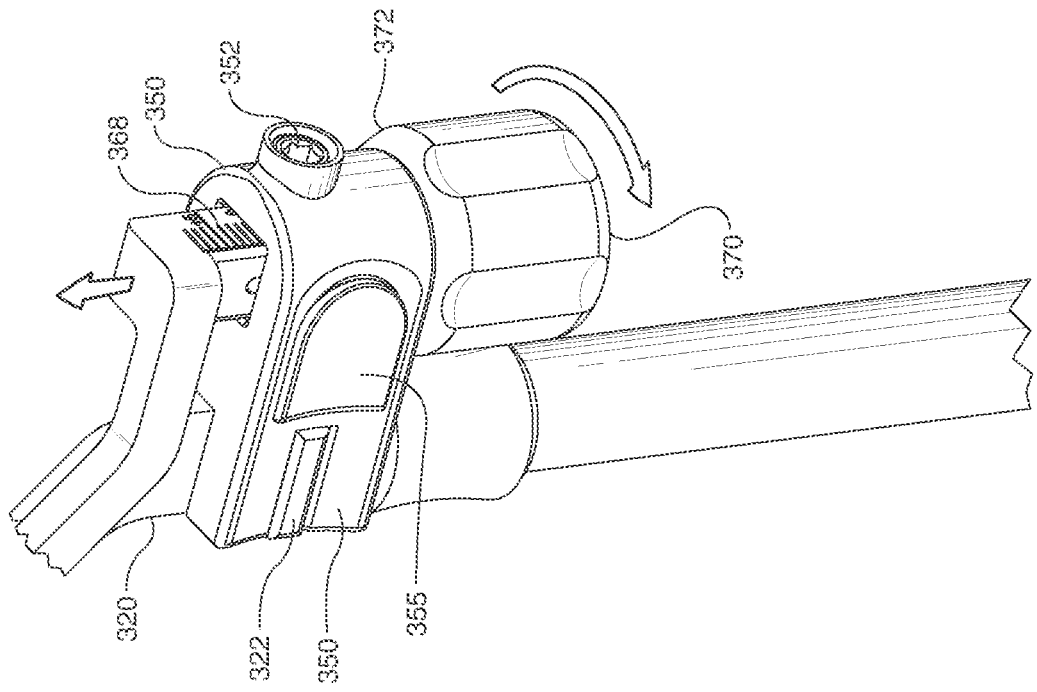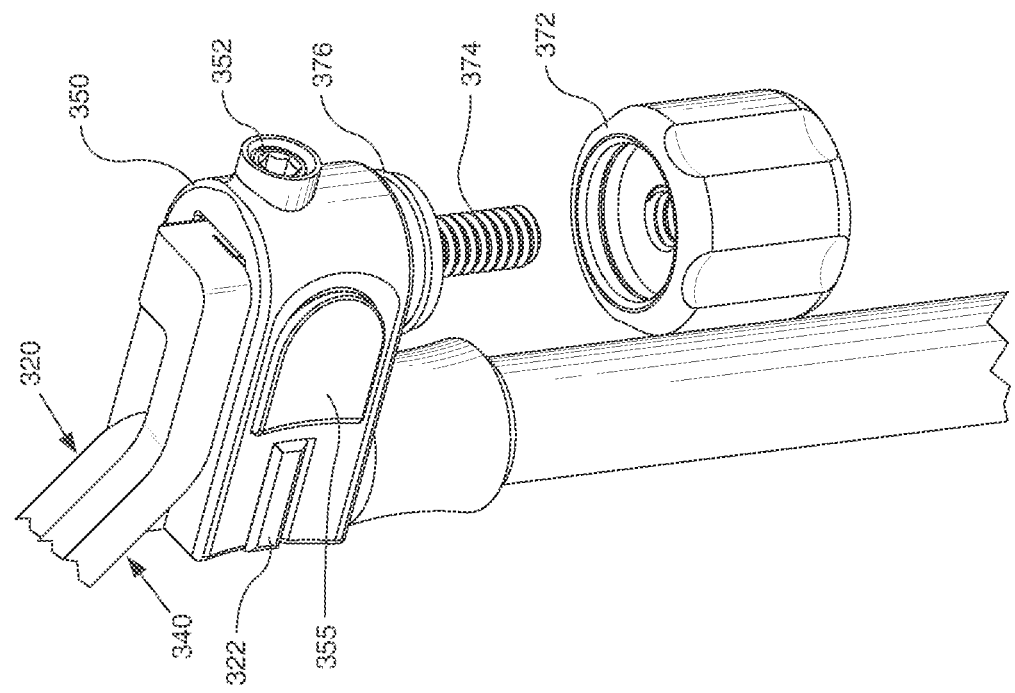

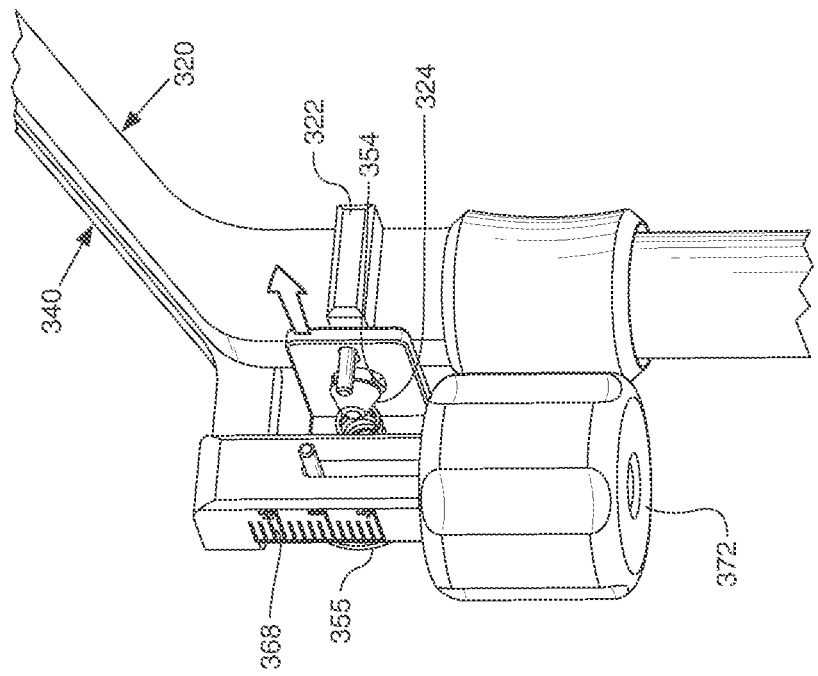
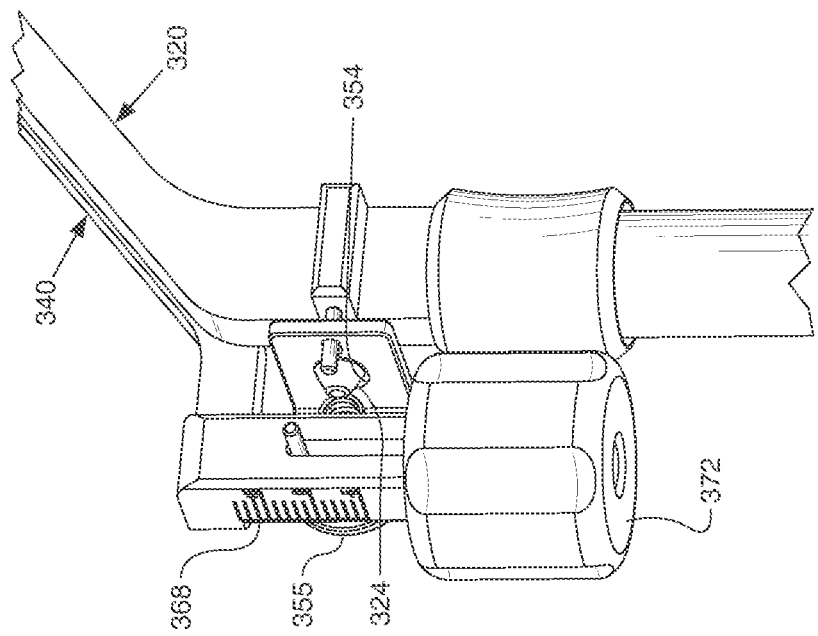

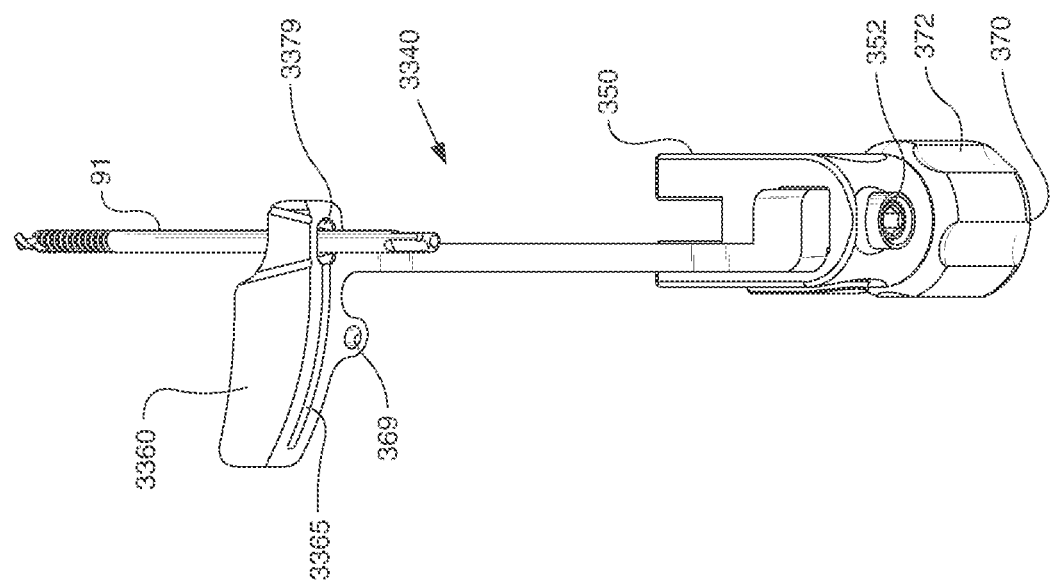
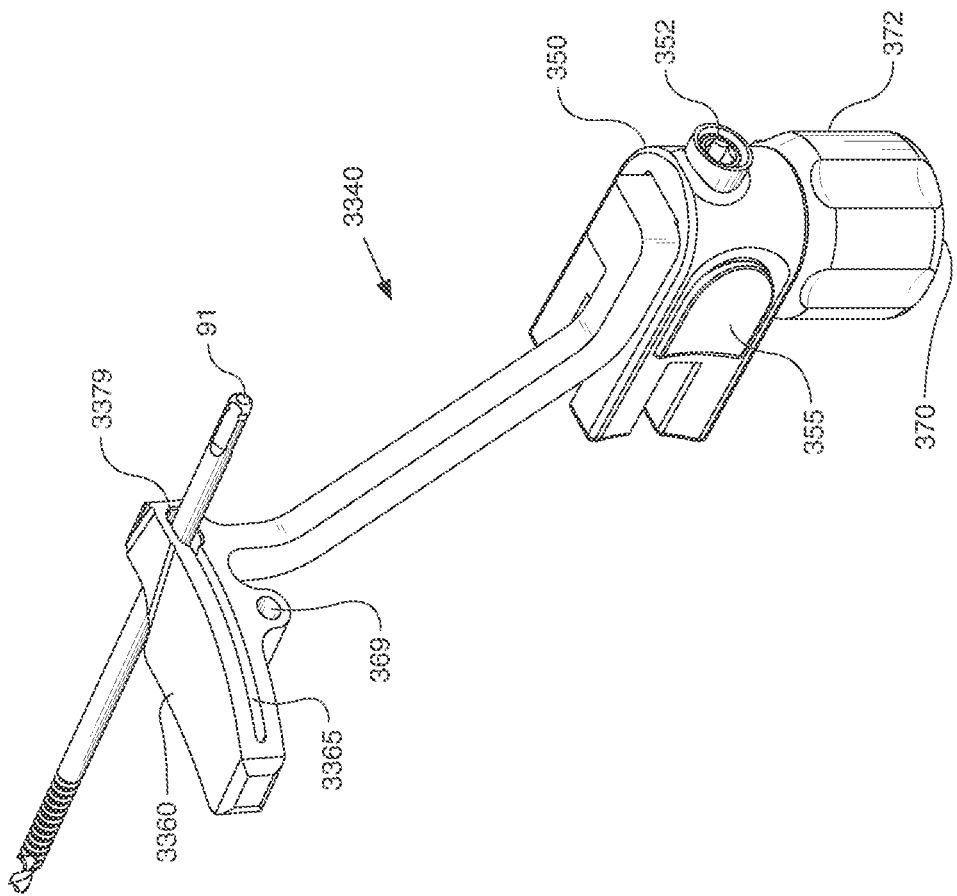

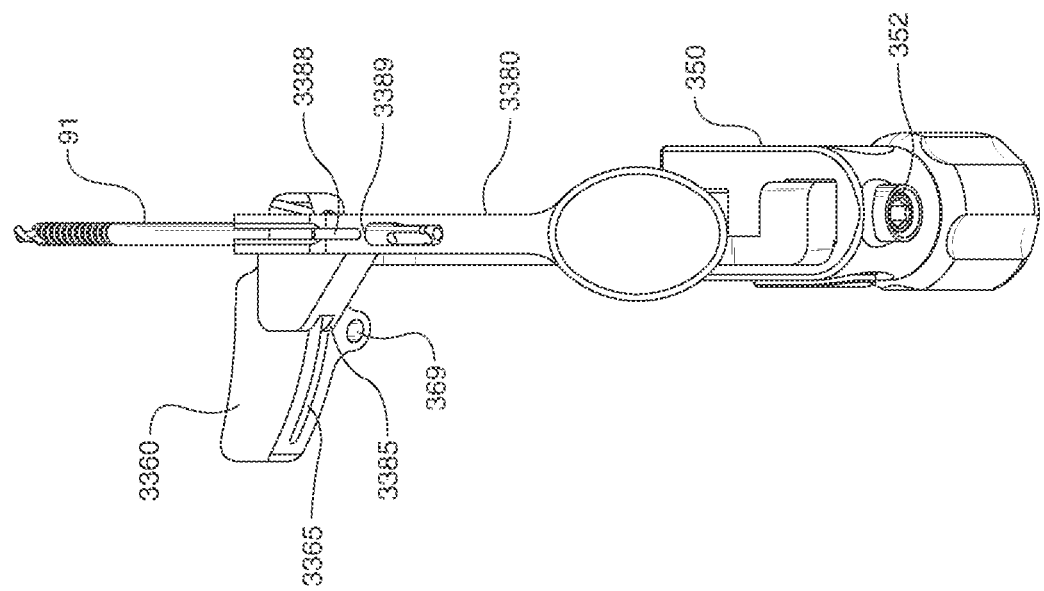
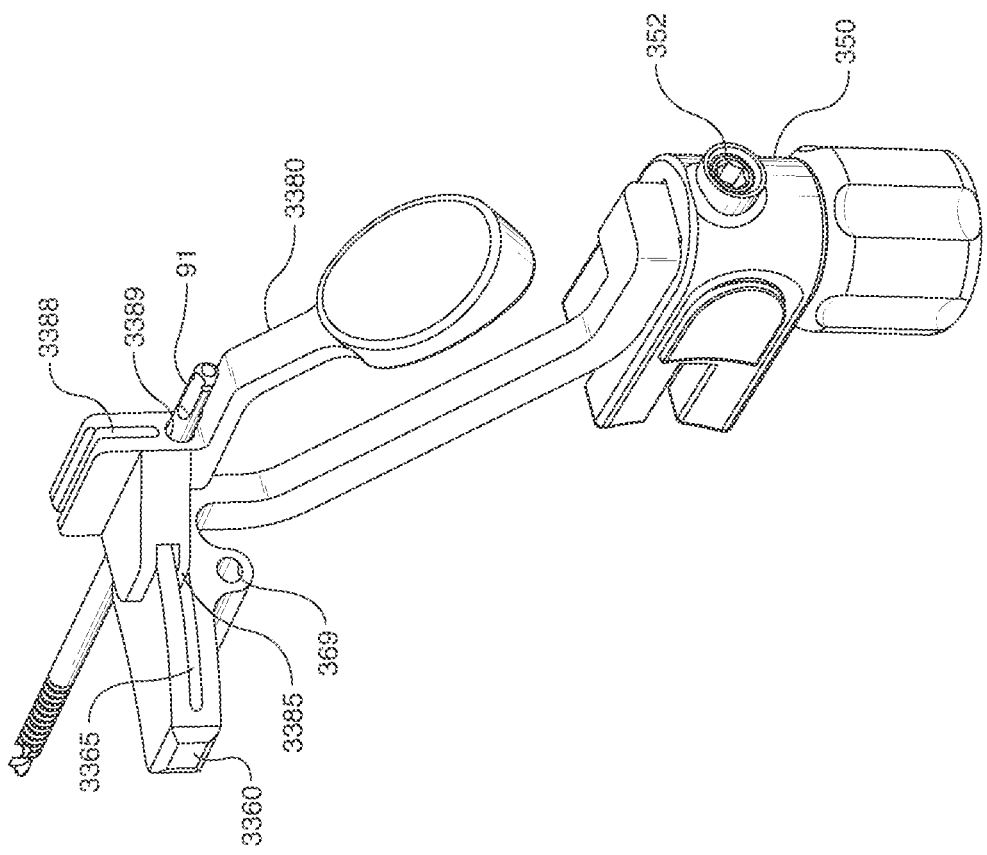
FIG. 31A
FIG. 31B

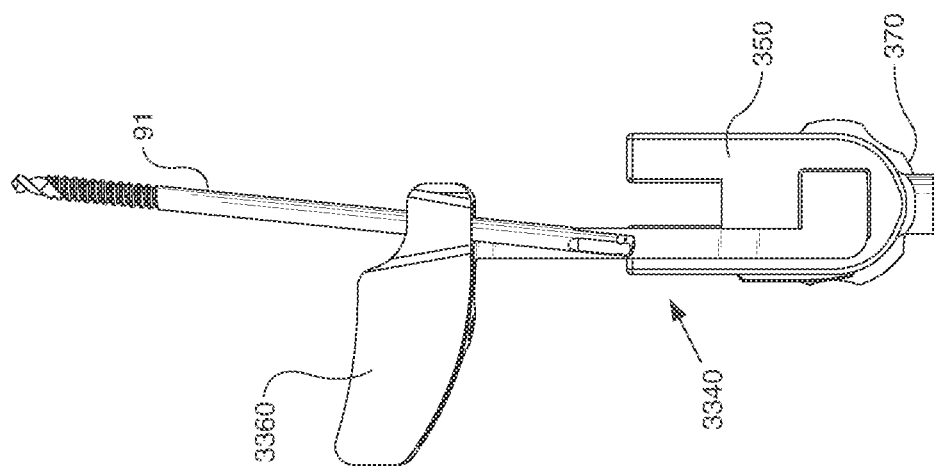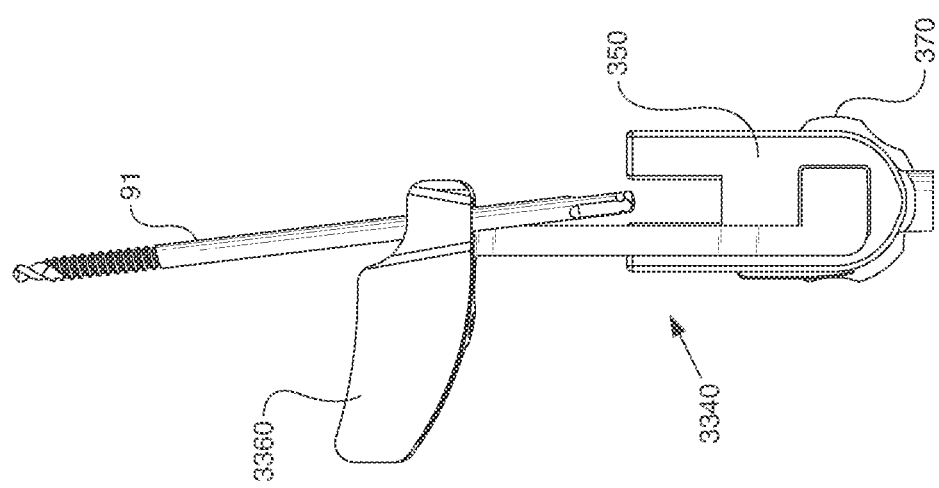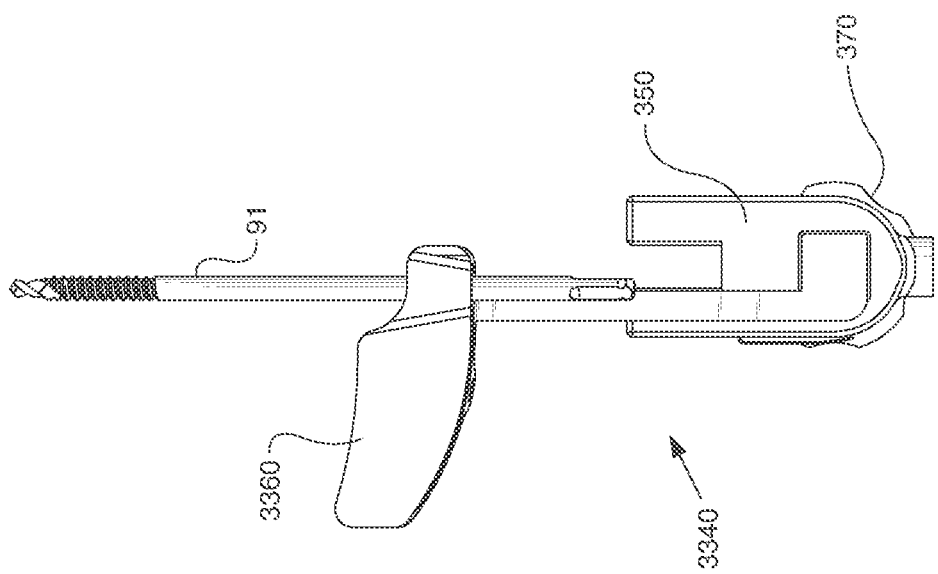

CUTTING GUIDE AND METHOD

CROSS-REFERENCE TO RELATED APPLICATIONS

This application is the U.S. national phase entry under 35 U.S.C. § 371 of International Application No. PCT/US2018/048727, filed Aug. 30, 2018, entitled "CUTTING GUIDE AND METHOD," which claims priority to and benefit of U.S. Provisional Application Ser. No. 62/635,383, filed Feb. 26, 2018, and U.S. Provisional Application Ser. No. 62/552,978, filed Aug. 31, 2017, the contents of each prior application is incorporated herein by reference in its entirety.

FIELD OF THE INVENTION

The present invention relates generally to the field of medical instruments, and more particularly relates to a cutting guide and method that may be used, for example, to prepare a tibia or femur to receive a knee arthroplasty implant such as a unicompartmental or total knee arthroplasty implant.

BACKGROUND

Knee arthroplasty procedures generally require resection of both a femur at its distal end and a tibia at its proximal end. Tibial cutting guides, for example, may be temporarily attached near a patient's ankle and near a proximal end of a tibia to provide support and guidance during cutting or other preparation. Accurate and controlled adjustment and fixation near the proximal end of the tibia, near the patient's ankle (often with an ankle clamp), and in the overall length of the instrument, may each be valuable in achieving accurate preparation for and placement of an arthroplasty device.

Near the proximal end of the tibia, it may be useful to have the ability to pin all or a portion of the instrument to the tibia, to fine-tune depth of resection (microadjustment), and to move part of the instrument out of the way to check the gap of the cut space while leaving the overall instrument pinned in place. This may permit more accurate re-cutting of the tibia if additional cutting of the tibia at a lower position than the previous cut is needed. It is a potential improvement to provide an instrument that has a removable part that may be reattached for re-cutting in a predictable and accurate manner. Removal and reattachment directly through a surgical incision may be useful to avoid damaging soft tissues in and around a patient's knee. It may also be valuable to have the ability to place an intersection pin at an intersection of a sagittal cut and a transverse cut for a unicondylar device at more than one location and angle relative to a cutting head. Some embodiments may include a modular capture device to locate and/or guide the sagittal cut.

During initial placement of the tibial cutting guide, both the proximal and distal ends need to be placed onto the patient's leg. An ergonomic problem with some current ankle clamps, at the distal end of the guide, is that the clamps' arms move independently of each other. This may cause difficulty in the initial handling and positioning of the instrument in surgery because the surgeon may have to use two hands to open the ankle clamp. It may be valuable to have the ability to operate the ankle clamp with one hand while stabilizing and positioning the other end of the guide with the other hand. Some prior art ankle clamps have used buttons that hold the arms open in a spring-loaded condition. Pressing the buttons could release the arms to a closed condition. This action could be performed with one hand by the surgeon, which was considered an advantage by some surgeons; however, the arms of some prior art devices closed with more force than was believed desirable. Therefore, a solution that allows for controlled single handed operation of a tibial guide ankle clamp would be a desirable solution.

Adjustment of the overall length of a cutting guide instrument is often difficult to achieve without a surgeon being required to use both hands during adjustment. It may be useful to equip an instrument with a hands-free sliding state to address this challenge. In addition, some surgeons prefer achieving the hands-free sliding state by engaging a push button that does not have to be held in place, as compared to, for example, being required to screw, unscrew, or move a nut, bolt, knob, or lever, or to hold a (spring-loaded) button down continuously. Some surgeons would prefer an instrument that has the capability to be left in a free-sliding or hands-free state while alignment at the ankle and near a proximal end of a tibia are achieved.

SUMMARY

An embodiment of the invention is a tibial cutting guide that includes at least a guide base, a cutting head, an alignment mechanism, and an ankle clamp. The cutting head may include a cutting head base, and a removable mechanism that includes at least a coupler releasably interconnectable with the cutting head base and configured to detach from the cutting head base upon activation, a blade guide, and a microadjustment element connected to the coupler and coupled to the blade guide, the microadjustment element being configured to move the blade guide to multiple positions relative to the coupler. The operation of the microadjustment element is independent from operation of the coupler between the cutting head base and the removable mechanism. The alignment mechanism may be coupled between the guide base and the cutting head and may include a body that couples with the guide base and the cutting head base, an engagement element movable relative to the body to selectively restrict or permit movement of the guide base relative to the cutting head base, and a mode selector configured to allow the engagement element to be selectively engaged and disengaged to restrict or permit movement of the guide base relative to the cutting head base when the mode selector is in a first state and configured to apply a force to the engagement element to urge the engagement element to continuously permit movement of the guide base relative to the cutting head base in a second state. The ankle clamp may be coupled to the guide base and include a housing, a first arm with a first pivot and two or more first gear teeth spaced along a radius from the first pivot, the first arm being pivotally coupled to the housing at the first pivot, and a second arm with a second pivot and two or more second gear teeth spaced along a radius from the second pivot, the second arm being pivotally coupled to the housing at the second pivot, and having its two or more second gear teeth interdigitating with the two or more first gear teeth of the first arm.

Another embodiment of the invention is an alignment mechanism that includes at least a body, an engagement element movable relative to the body to restrict or permit movement of the body relative to a member to which the engagement element is configured to couple, and a mode selector configured to allow the engagement element to engage and disengage when the mode selector is in a first state and configured to apply a force to the engagement element to urge the engagement element to be disengaged in a second state.

Yet another embodiment of the invention is an alignment mechanism configured to function in three operating conditions. Alignment mechanism embodiments include an engagement element capable of contacting a portion of another component to stop movement between the other component and the engagement element, and a mode selector. The mode selector when in a first state permits two operating conditions: a) a condition where force is not being applied to the engagement element by a user and the engagement element is in contact with a portion of another component, and b) a condition where force is being applied to the engagement element by a user and the engagement element is not in contact with a portion of another component. When the mode selector is in a second state, it permits only one operating condition: c) a condition where regardless of whether force is being applied to the engagement element by a user, the engagement element is not in contact with a portion of another component.

Still another embodiment of the invention is a cutting head that includes at least a cutting head base and a removable mechanism. The removable mechanism may include a coupler releasably interconnectable with the cutting head base and configured to detach from the cutting head base upon activation, a blade guide, and a microadjustment element connected to the coupler and coupled to the blade guide, the microadjustment element being configured to move the blade guide to multiple positions relative to the coupler. Operation of the microadjustment element of some embodiments is independent from operation of the coupler between the cutting head base and the removable mechanism.

An embodiment of the invention is a blade guide that includes a body. The body may also include an opening in the body sized and oriented to direct a blade by having a substantially close fit between a wider proportion side of the blade and the opening. The opening may also have a greater longitudinal direction and a lesser height substantially perpendicular to the longitudinal direction. The body may also include a pin slot in the body having a width in substantially the same direction as the longitudinal direction of the opening and a height less than the width. The pin slot of some embodiments is sized to have a substantially close fit between its height and a pin configured to be inserted through the pin slot and a looser fit between its width and the pin such that the pin is able to be moved along the width of the pin slot and pivot about an axis parallel to the height of the pin slot.

Another embodiment of the invention is an ankle clamp with a housing, a first arm, and a second arm. The first arm may include a first pivot and two or more first gear teeth spaced along a radius from the first pivot, the first arm being pivotally coupled to the housing at the first pivot. The second arm may include a second arm with a second pivot and two or more second gear teeth spaced along a radius from the second pivot, the second arm being pivotally coupled to the housing at the second pivot, and having its two or more second gear teeth interdigitating with the two or more first gear teeth of the first arm.

A method embodiment of the invention is directed to positioning a cutting guide and resecting a patient's tibia. Acts of the method may include moving a mode selector to a position that allows free length movement of the cutting guide, opening two arms of a clamp away from a center of the clamp by moving one of the arms away from the center of the clamp, placing the clamp on the patient's ankle, and closing the two arms of the clamp by moving one of the arms toward the center of the clamp. The method may also include adjusting a length of the cutting guide to place an at least two piece cutting head of the cutting guide adjacent to the tibia, moving the mode selector to a position that does not allow free length movement to set the cutting guide length, attaching a first portion of the cutting head to the tibia, and cutting the tibia through a second portion of the cutting head that is adjustable relative to the first portion of the cutting head and removable relative to the first portion of the cutting head. If desired, the method may optionally include removing the second portion of the cutting head relative to the first portion of the cutting head to better visualize the tibia. If desired, the method may optionally include replacing the second portion of the cutting head onto the first portion of the cutting head, adjusting the second portion of the cutting head relative to the first portion of the cutting head, and cutting the tibia through the second portion of the cutting head.

Yet another method embodiment of the invention includes length adjustment of a cutting guide with an alignment mechanism configured to function in three operating conditions. An act of the method may include locating a mode selector in a location defining a first state that permits two operating conditions: a) a condition where force is not being applied to an engagement element of the alignment mechanism by a user and the engagement element is in contact with a portion of another component, and b) a condition where force is being applied to the engagement element by a user and the engagement element is not in contact with a portion of another component. In this condition where force is applied to the engagement element, length adjustment of the cutting guide is accomplished by pulling or pushing ends of the cutting guide apart or together while force is being applied to the engagement element by a user. The method may also include locating the mode selector in a location defining a second state that permits an operating condition defined as: c) a condition where regardless of whether force is being applied to the engagement element by a user, the engagement element is not in contact with a portion of another component, and wherein in this condition length adjustment of the cutting guide is accomplished by pulling or pushing ends of the cutting guide apart or together.

Still another method embodiment of the invention includes positioning a two-part cutting head having a cutting head base and a removable mechanism relative to a tibia, the method including at least the acts of coupling the cutting head base to the tibia; and choosing to alter the position of the removable mechanism relative to the cutting head base if a blade guide of the removable mechanism is not in a desired location relative to the tibia by altering a microadjustment element. Optionally, the method may include detaching the removable mechanism from the cutting head base to better visualize the tibia behind the removable mechanism. Optionally, the method may include returning the removable mechanism to the cutting head base, wherein when returned to the cutting head base the blade guide of the removable mechanism is in the same location as when detached from the cutting head base.

Another embodiment of the invention is a method of operating an ankle clamp of a cutting guide with a housing and a first arm and a second arm. The method may include moving the first arm with a first pivot and two or more first gear teeth spaced along a radius from the first pivot, the first arm being pivotally coupled to the housing at the first pivot, away from a center of the ankle clamp. Movement of the first arm away from the center of the ankle clamp about the first pivot may cause the second arm that has a second pivot and two or more second gear teeth spaced along a radius from the second pivot, the second arm being pivotally coupled to the housing at the second pivot, and having its two or more second gear teeth interdigitating with the two or more first gear teeth of the first arm to also move away from a center of the ankle clamp while pivoting about the second pivot.

Another method embodiment of the invention is a method of positioning a cutting guide and resecting a patient's tibia in preparation for placing a unicondylar tibial implant. The method may include attaching a clamp of a cutting guide at or near the patient's ankle and adjusting the cutting guide to position a cutting head with a blade guide to align the blade guide to a location where a transverse cut in the patient's tibia can be made through the blade guide. The method may also include attaching a portion of the cutting head to the patient's tibia and identifying relative to the cutting head an angle of insertion and a medial-lateral location for an intersection pin that is to be placed through a pin slot in the blade guide, wherein the intersection pin is to be placed along a trajectory that defines an extent of a transverse cut to be made in the tibia where the transverse cut is to intersect with a sagittal cut to be made in the tibia. The method may also include placing an intersection pin in the tibia through the pin slot in the blade guide at the identified angle, making the sagittal cut using the intersection pin as a stop, and making the transverse cut through the blade guide using the intersection pin as a stop.

BRIEF DESCRIPTION OF THE DRAWINGS

FIG. 6 is a perspective view of a portion of the guide base and the alignment mechanism with the mode selector in a first state and with the engagement element disengage from the guide base.

FIG. 7 is a perspective view of the guide base and the alignment mechanism illustrated in FIG. 6 with the body of the alignment mechanism removed for clarity to illustrate operation of the mode selector and engagement element.

FIG. 8 is a perspective view of a portion of the guide base and the alignment mechanism with the mode selector in a second state that forces the engagement element to be disengage from the guide base.

FIG. 9 is a perspective view of the guide base and the alignment mechanism illustrated in FIG. 8 with the body of the alignment mechanism removed for clarity to illustrate operation of the mode selector and engagement element.

FIG. 11 is a partially exploded perspective view of a portion of the cutting head of FIG. 10.

FIG. 12 is perspective view of a portion of the cutting head of FIG. 10 shown in operation.

FIG. 14 is a perspective view of a portion of the cutting head, with some components of the cutting head removed for clarity, showing the device prior to activation that would allow the removable mechanism may be removed from the cutting head base.

FIG. 15 is a perspective view of a portion of the cutting head, with some components of the cutting head removed for clarity, showing the device after activation that allows the removable mechanism to be removed from the cutting head base.

FIG. 30A is a perspective view of the removable mechanism of the cutting head with an intersection pin.

FIG. 30B is an alternate perspective view of the removable mechanism of the cutting head with the intersection pin shown in FIG. 30A.

FIG. 31A is a perspective view of the removable mechanism of the cutting head with an intersection pin and a modular capture device.

FIG. 31B is an alternate perspective view of the removable mechanism of the cutting head with the intersection pin and the modular capture device shown in FIG. 31A

FIG. 32A is a plan view of the removable mechanism of the cutting head with an intersection pin shown at a first angle of insertion and medial-lateral location relative the blade guide.

FIG. 32B is a plan view of the removable mechanism of the cutting head with an intersection pin shown at a second angle of insertion and medial-lateral location relative the blade guide.

FIG. 32C is a plan view of the removable mechanism of the cutting head with an intersection pin shown at a third angle of insertion and medial-lateral location relative the blade guide.

DETAILED DESCRIPTION

Figure 1:
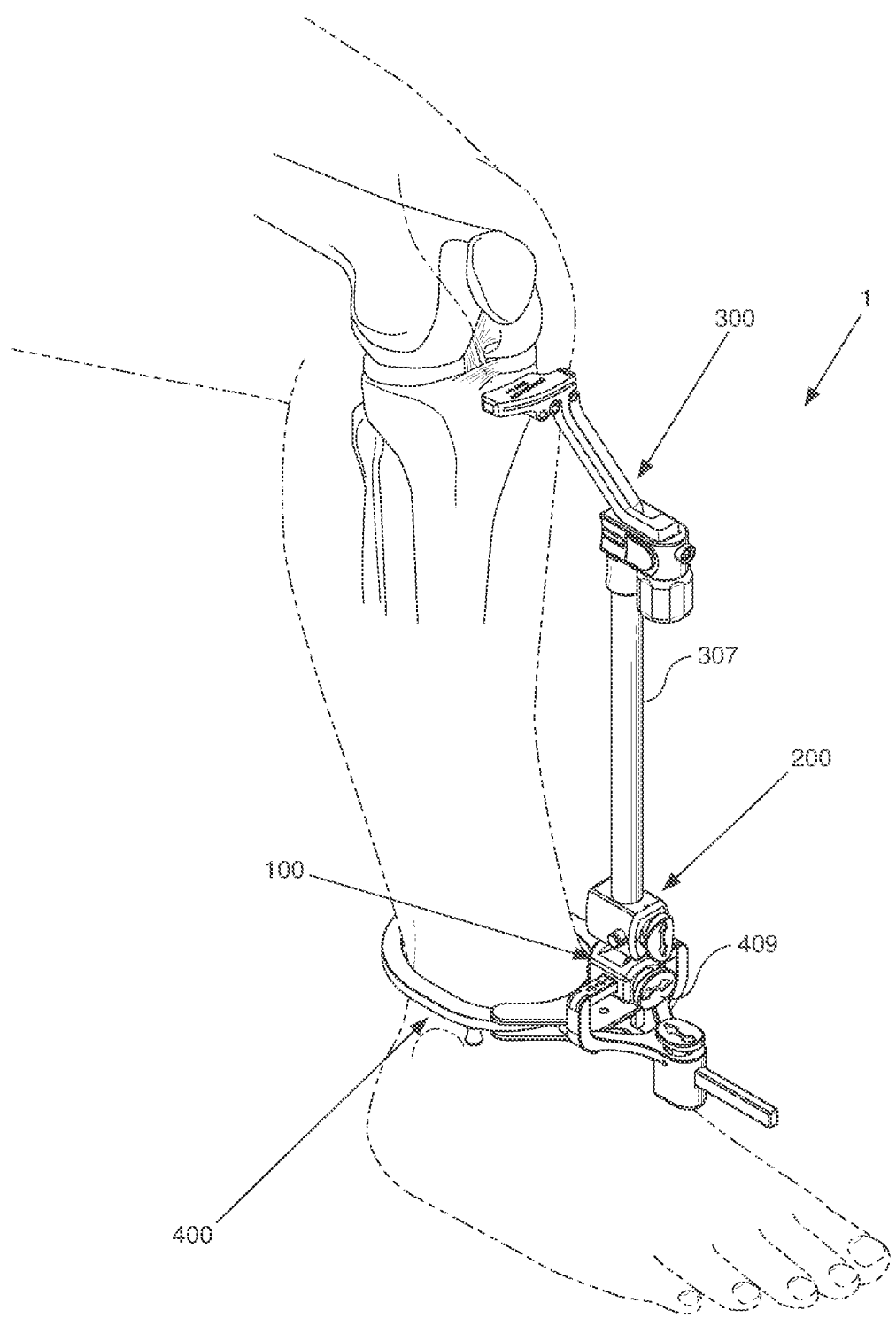
FIG. 1 is a perspective view of an embodiment of the cutting guide in place on a patient's leg (patient's leg drawn with phantom lines).

A tibial cutting guide 1 is illustrated in FIG. 1 coupled to the leg of a patient (the patient's leg is drawn with phantom lines). The tibial cutting guide 1 illustrated includes a guide base 100, an alignment mechanism 200, a cutting head 300, and an ankle clamp 400. The alignment mechanism 200 is movably coupled to the guide base 100.

Figure 2:
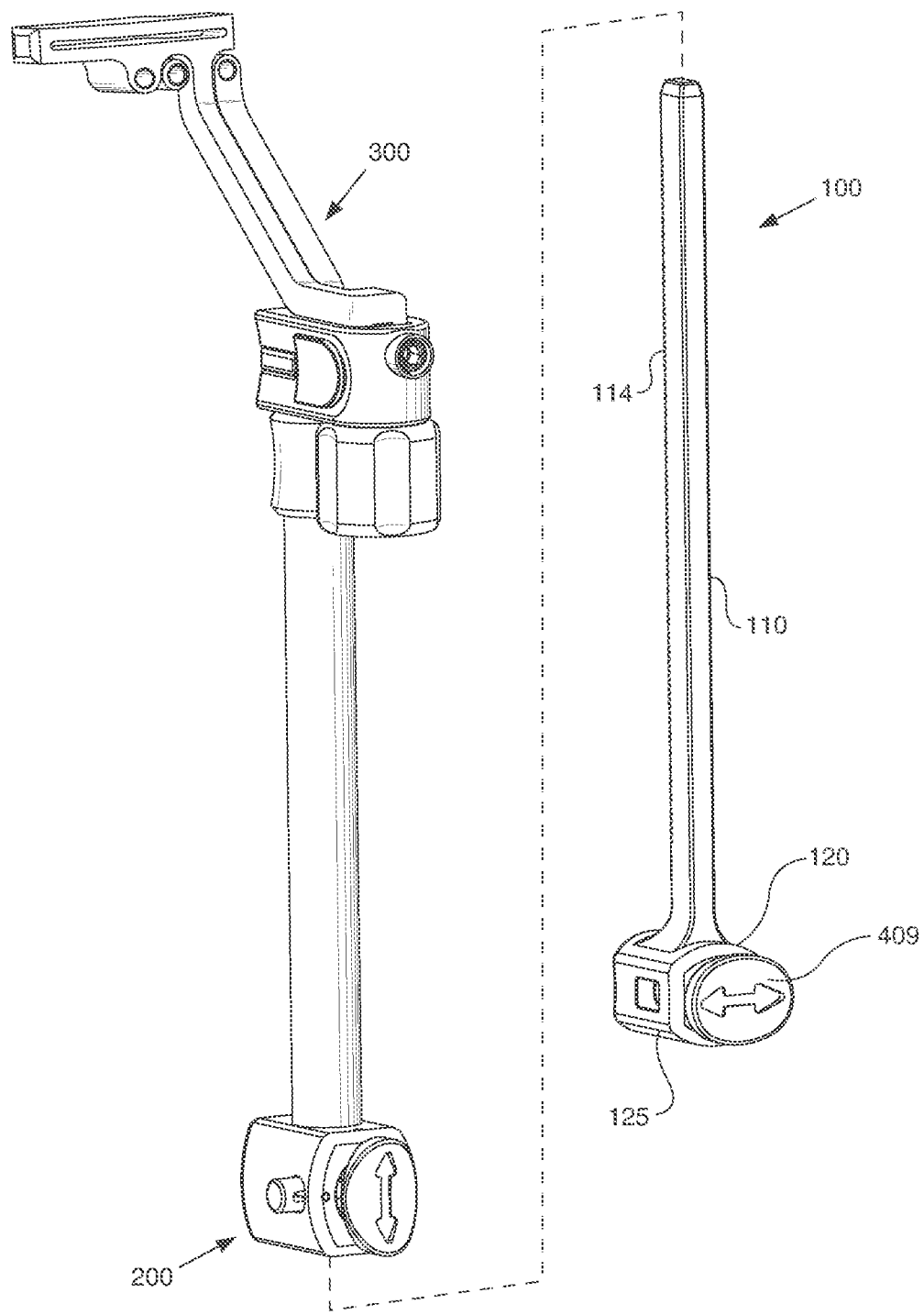
FIG. 2 is an exploded perspective view of portions of the cutting guide of FIG. 1.

The guide base 100 is shown in the illustrated embodiment with a shaft 110 and a collar 120, as most clearly illustrated in FIG. 2. FIG. 2 is an exploded perspective view showing the guide base 100 and the cutting head 300, but omitting the ankle clamp 400 for clarity. The shaft 110 is configured to penetrate through at least a portion of the alignment mechanism 200, as illustrated in FIG. 1. The illustrated shaft 110 has a rectangular cross-section and includes teeth 114 on at least one side of the rectangular cross-section. The teeth 114 are configured to interact with an engagement element 220 as illustrated, for example, in FIG. 5 at teeth 224 of the engagement element 220. Any other functional cross-section for a shaft may be used in other embodiments. The collar 120 includes an opening 125 (FIG. 2) through which a connection element of the ankle clamp 400, such as a bracket 408 illustrated in FIG. 17, may be passed. In the illustrated embodiment, sliding of the collar 120 of the guide base 100 is regulated by pressing of the button 409 (FIGS. 1 and 2). Specifically, in this example when the button 409 is pressed, the collar 120 is free to slide along the bracket 408, and when the button 409 is released, the collar 120 is prevented from sliding along the bracket 408. Any other functional type of connection mechanism may be used in other embodiments, including for example and without limitation a rack and pinion system, a setscrew, a threaded mechanism, worm gear system, or an automated drive system.

Figure 3:
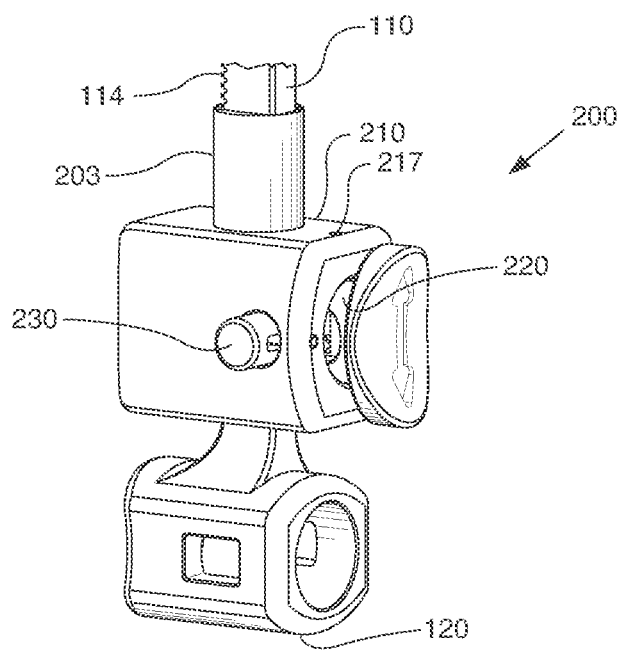
FIG. 3 is a perspective view of a portion of the guide base and the alignment mechanism with the mode selector in a first state and with the engagement element engaged with the guide base.
Figure 4:
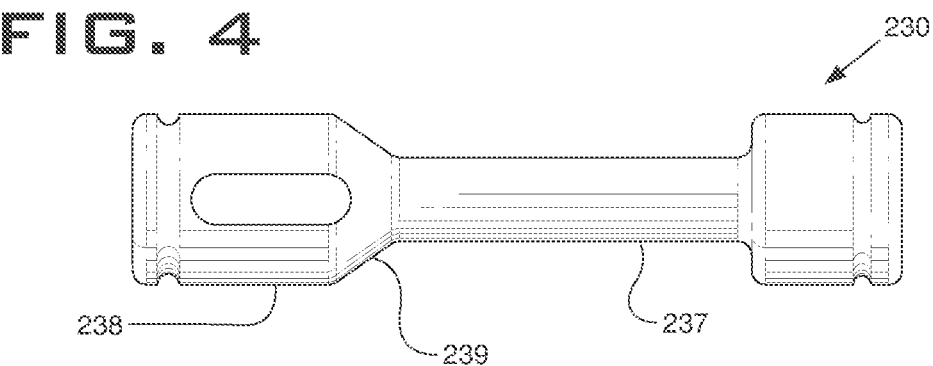
FIG. 4 is an elevation view of the mode selector of the alignment mechanism illustrated in FIG. 3.

The alignment mechanism 200 shown in FIGS. 3-9 in various states of operation has a body 210 and an engagement element 220. The engagement element 220 depicted is movable relative to the body 210 to engage with and disengage from the guide base 100 to restrict or permit movement of the body 210 relative to the guide base 100. A portion 203 of the body 210 is tubular to receive the shaft 110 of the guide base 100. As shown in FIGS. 3, 6, and 8, the tubular portion 203 of the body 210 is substantially rectangular about its inner portion and is round around its outer portion. As shown in FIG. 1, the alignment mechanism 200 may be coupled with a tubular portion 307 of the cutting head 300. This coupling may be permanent or temporary. The portion 203 of the body 210 that is tubular may be any other functional shape in other embodiments. For example and without limitation, the cross-section may be the same or dissimilar about the inner portion or the outer portion and may be round, rectangular, or any other polygonal, fully enclosed, or partially enclosed shape.

Figure 5:
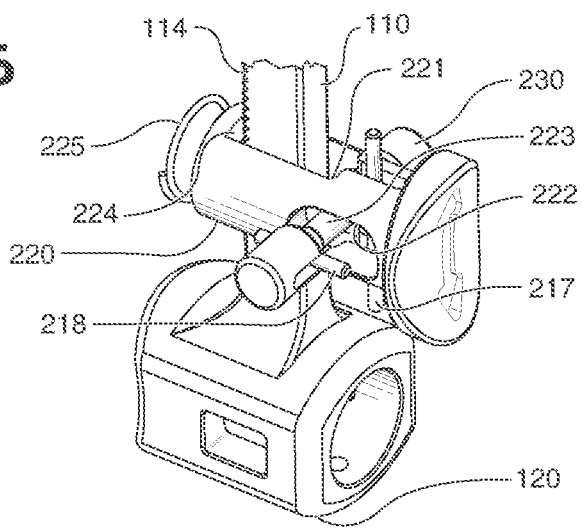
FIG. 5 is a perspective view of the guide base and the alignment mechanism illustrated in FIG. 3 with the body of the alignment mechanism removed for clarity to illustrate operation of the mode selector and engagement element.

As illustrated in FIGS. 3-9, a mode selector 230 is configured to allow the engagement element 220 to engage and disengage from the guide base 100 when the mode selector 230 is in a first state (FIGS. 3, 5-7). The mode selector 230 is also configured to apply a force to the engagement element 220 to urge the engagement element 220 to disengage from the guide base 100 in a second state (FIGS. 8-9). The engagement element 220 includes teeth 224 configured to engage with the teeth 114 of the guide base 100 to restrict movement of the body 210 relative to the guide base 100, as depicted in FIG. 5. In addition or as an alternative to teeth, any other effective engagement elements may be used in other embodiments to selectively allow or restrict movement between a guide base and an alignment mechanism. As shown in FIGS. 5, 7, and 9 the engagement element 220 includes a first opening 221 configured to receive a portion of the guide base 100. The illustrated engagement element 220 also includes a second opening 222 configured to receive the mode selector 230.

The mode selector 230 shown in FIGS. 3-9 fits through the engagement element 220 to interact with an interior portion 223 (FIG. 9) of the engagement element 220. The mode selector 230 depicted has a cylindrical cross-section of varying diameters along its length. In other embodiments, the cross-section may be rectangular or any other functional shape. As most clearly seen in FIG. 4, the mode selector 230 includes a smaller diameter 237 and a larger diameter 238 with a transition portion 239 between the smaller diameter 237 and the larger diameter 238. When the smaller diameter 237 of the mode selector 230 aligns with the interior portion 223 of the engagement element 220, the engagement element may be engaged and disengaged from the guide base 100—the first state of the mode selector 230 (FIGS. 3, 5-7). When the larger diameter 238 of mode selector 230 aligns with the interior portion 223 of the engagement element 220, the mode selector 230 applies a force to the engagement element 220 to urge the engagement element 220 to disengage from the guide base 100—the second state of the mode selector 230 (FIGS. 8 and will 9). The transition portion 239 of the mode selector 230 is sloped at a rate that is desirable to facilitate ergonomic operation of the mode selector 230. In other words, the slope is not so short and steep that the button is too difficult to push; and the slope is not so long and shallow that an uncomfortable or inconvenient mode selector travel would be required. In other embodiments, a mode selector may be a rotatable object rather than a sliding object wherein it is asymmetrical about its center of rotation such that rotation to different angles creates different degrees of movement of an engagement element.

In the illustrated embodiment, the alignment mechanism 200 also includes an engagement biasing element 225 (FIGS. 5, 7, and 9) that presses the engagement element 220 toward contact with the guide base 100. The engagement biasing element 225 shown is a coil spring but in other embodiments may be any other effective biasing element, including but not limited to, a leaf spring or an elastomeric component. As shown in FIGS. 3 and 5-9, the alignment mechanism 200 includes a guidance pin 217 that passes through a wall of the body 210 to guide and limit the travel of the engagement element 220 during its operation. Similarly, a guidance pin 218 passes through the wall of the body 210 to guide and limit the travel of the mode selector 230 during its operation (FIGS. 5, 7, and 9).

The illustrated alignment mechanism 200 is disclosed as a part of the tibial cutting guide 1. However, in other embodiments, an alignment mechanism within the scope of the disclosure herein may be an independently operating device or a component of another system that does not necessarily involve alignment for the resection of a tibia in preparation for an arthroplasty device.

Figure 10:
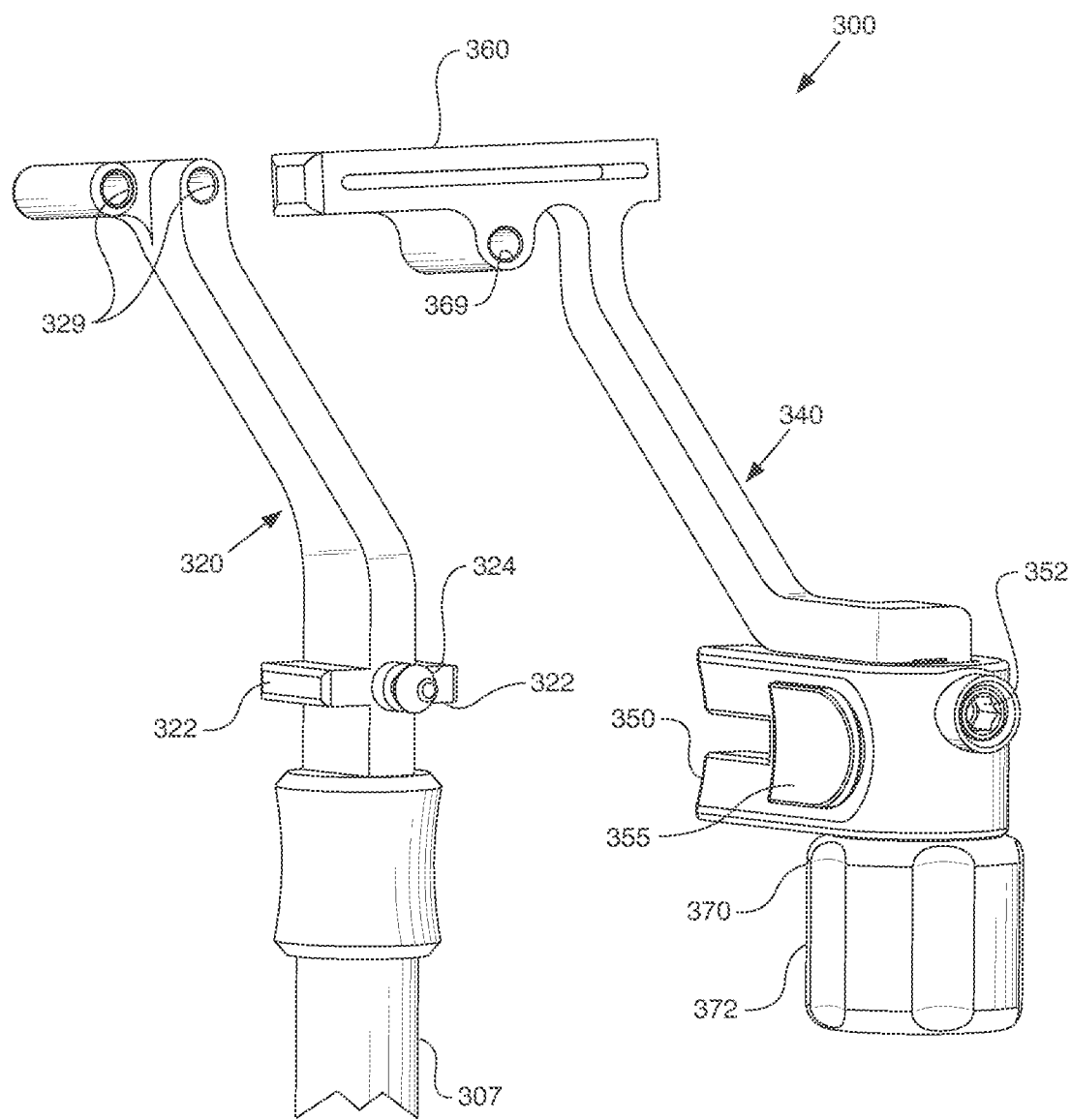
FIG. 10 is a partially exploded perspective view of a cutting head of the cutting guide of FIG. 1.
Figure 13:
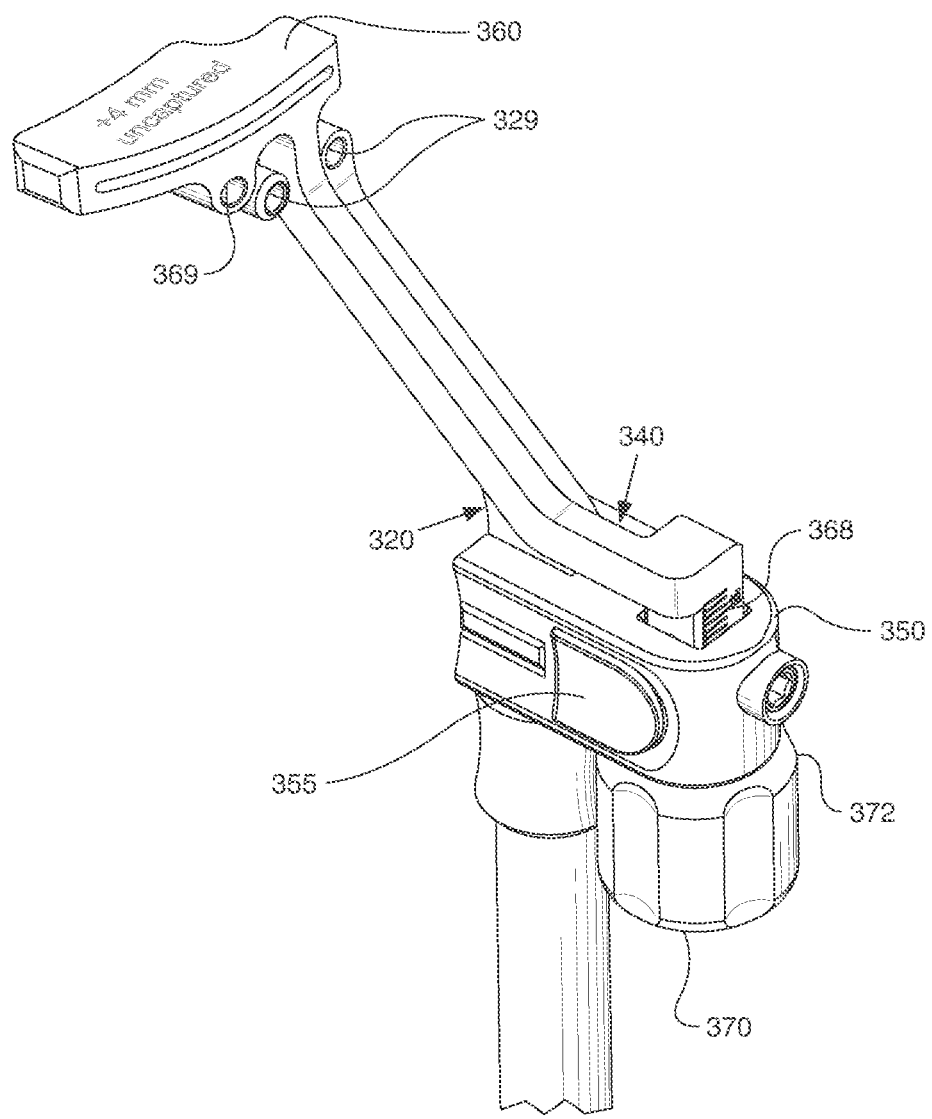
FIG. 13 is a perspective view of the cutting head as adjusted in FIG. 12 and showing the removable mechanism relative to the cutting head base, as adjusted.
Figure 16:
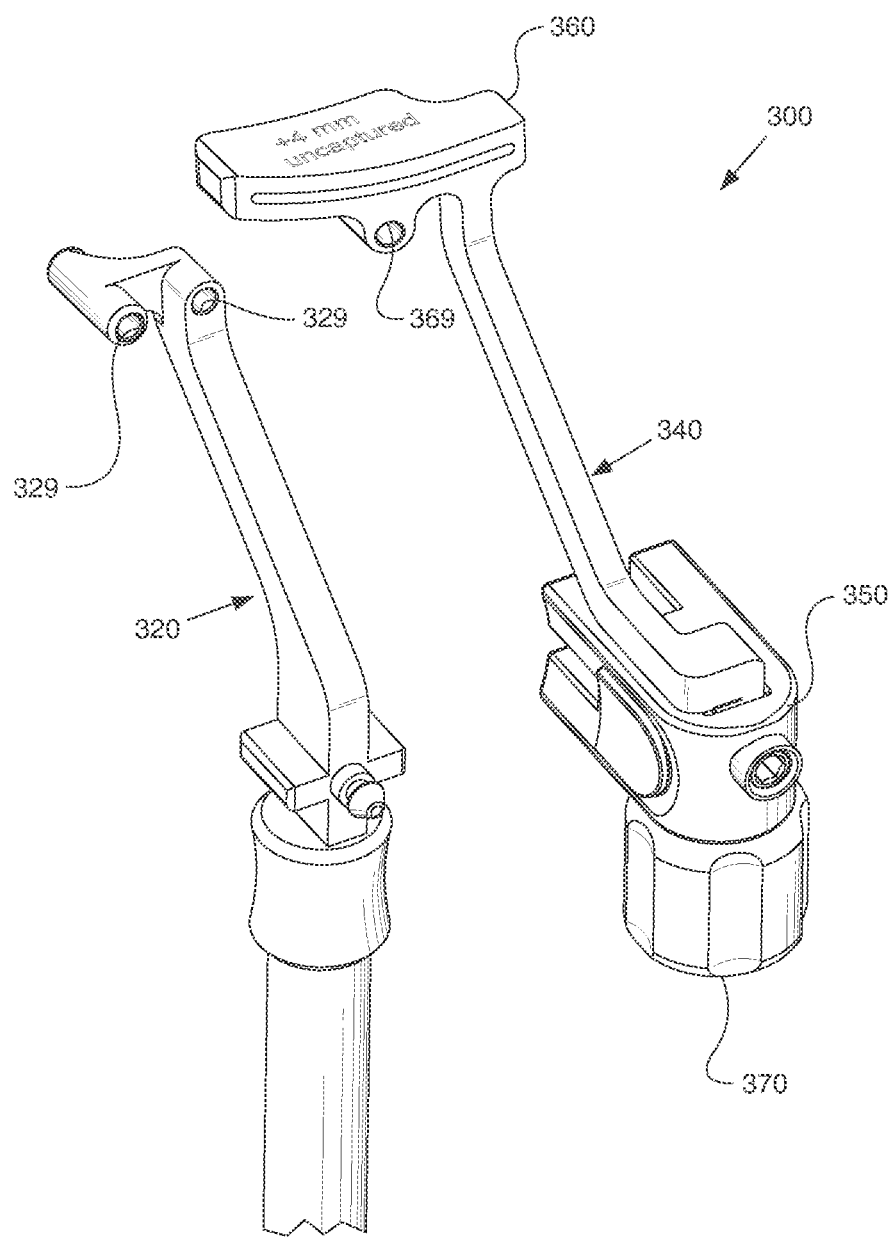
FIG. 16 is a perspective view of a portion of the cutting head showing the removable mechanism removed from the cutting head base.

As shown in FIG. 10, the cutting head 300 depicted is coupled to the alignment mechanism 200 through the tubular portion 307 of the cutting head 300. The cutting head 300 illustrated in more detail in FIGS. 10-16 includes a cutting head base 320 coupled to the alignment mechanism 200 and a removable mechanism 340 that includes a coupler 350 releasably interconnectable with the cutting head base 320 and configured to detach from the cutting head base 320 upon activation. The coupler 350 of the removable mechanism 340 includes a push portion 355 that disengages a latch 354 from a connection 324 on the cutting head base 320 (see the progression from FIG. 14 to FIG. 15). The illustrated connection between the cutting head base 320 and the removable mechanism 340 also includes rails 322 on the cutting head base 320 that fit into a slot in the coupler 350. Disengaging the latch 354 from the connection 324 allows the removable mechanism 340 to be separated from the cutting head base, as illustrated in FIGS. 10 and 16. Any other effective latch or capture mechanism may be used in embodiments of the invention. The embodiment of the cutting head base 320 shown includes two pin holes 329 for receiving one or more fasteners by which the cutting head base 320 may be coupled with the tibia. The one or more fasteners may be pins, screws, staples, or any functional fastener device.

The removable mechanism 340 shown also includes a blade guide 360, and a microadjustment element 370 connected to the coupler 350 and coupled to the blade guide 360. Embodiments of the blade guide may be adapted to direct a blade through only a portion of the tibia aligning with a single condyle landing area of the knee joint to facilitate preparation of a unicondylar knee implant. For example, a slot in the blade guide may limit the lateral travel or the angle of application of a blade capable of fitting through the blade guide, thereby directing the blade or only a portion of a tibia to which the device is been attached. The term "single condyle landing area" is intended to refer to the portion of a tibia to which a single condyle of a femur would substantially align when a knee is functioning properly. Other blade guides may be arranged, without limitation, to perform a total knee arthroplasty. The microadjustment element 370 of some embodiments is configured to move the blade guide 360 to multiple positions relative to the coupler 350. As shown in FIGS. 10-16, the microadjustment element 370 includes a knob 372, a lift bolt 374, and a retainer ring 376. The knob 372 in the illustrated embodiment is configured to rotate freely about the retainer ring 376 and therefore to drive the lift bolt 374 (and the blade guide 360, to which the lift bolt 374 is coupled) relative to the coupler 350. As shown by the action arrows in FIG. 12, counterclockwise rotation of the knob 372 causes lifting or extension of the blade guide 360 away from the coupler 350 and consequently the cutting head base 320. By this operation the microadjustment element 370 moves the blade guide 360 substantially parallel with an axis moved by the alignment mechanism 200 relative to the guide base 100. Indicia 368 (FIGS. 12-15) on a lower portion of the blade guide 360 near where the lift bolt 374 is coupled, graphically represent the relative distance movements between the blade guide 360 and the coupler 350. When a desired position for the blade guide 360 is obtained relative to the coupler 350, a set screw 352 may be tightened to fix the position of the blade guide 360 relative to the coupler 350. The blade guide 360 also includes a pin hole 369, and in other embodiments may include more than one, for receiving one or more fasteners by which the blade guide 360 may be coupled with the tibia. The one or more fasteners may be pins, screws, staples, or any functional fastener device. Operation of the microadjustment element 370 is independent from operation of the coupler 350 between the cutting head base 320 and the removable mechanism 340.

The illustrated cutting head 300 is disclosed as a part of the tibial cutting guide 1. However, in other embodiments, a cutting head within the scope of the disclosure herein may be an independently operating device or a component of another system that does not necessarily involve alignment for the resection of a tibia in preparation for an arthroplasty device.

Figure 21:
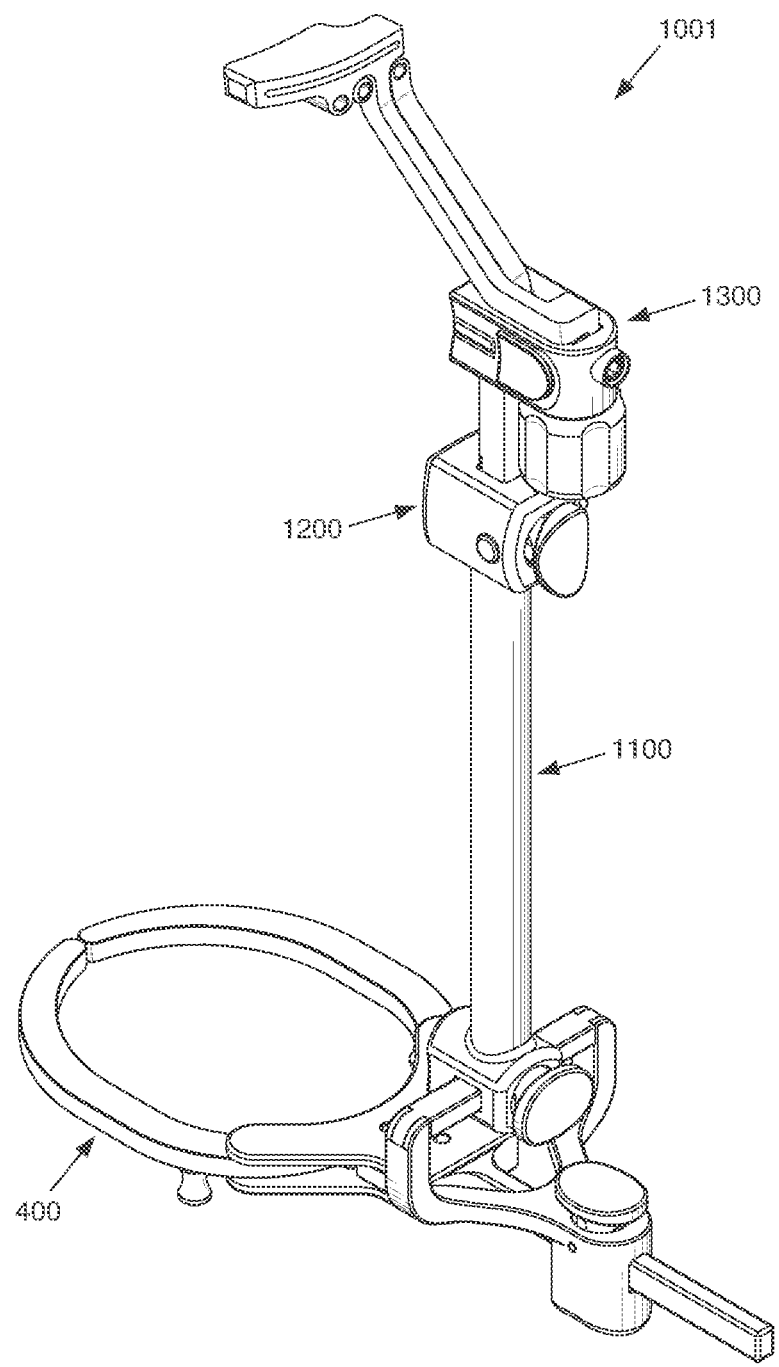
FIG. 21 is a perspective view of another embodiment of the cutting guide.
Figure 22:
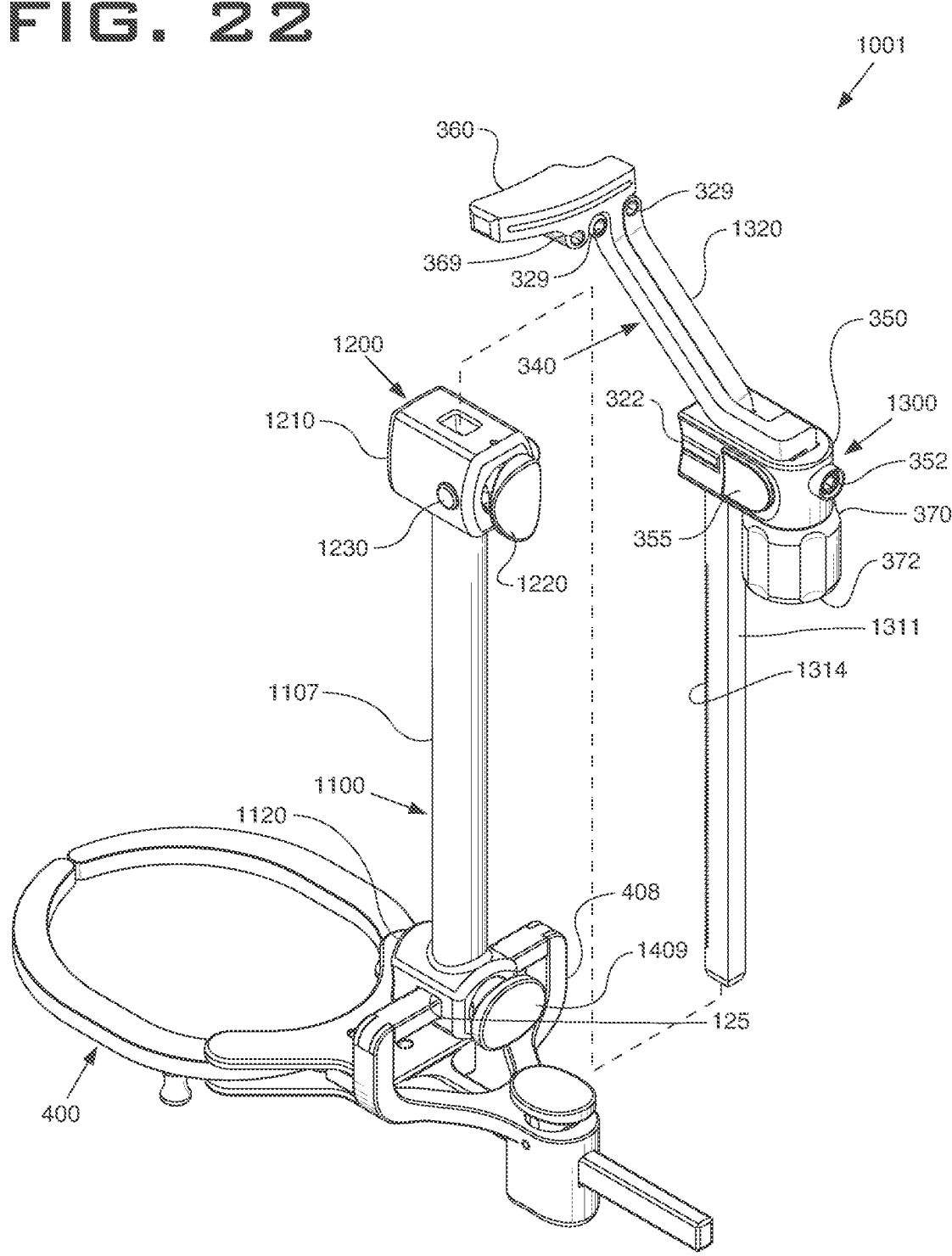
FIG. 22 is a partially exploded perspective view of portions of the cutting guide of FIG. 21.

A tibial cutting guide 1001 is illustrated in FIGS. 21 and 22. The tibial cutting guide 1001 illustrated includes a guide base 1100, an alignment mechanism 1200, a cutting head 1300, and an ankle clamp 400. The alignment mechanism 1200 is movably coupled to the cutting head 1300.

The guide base 1100 is shown in the illustrated embodiment with a tubular portion 1107 and a collar 1120, as illustrated in FIG. 22. FIG. 22 is a partially exploded perspective view showing the alignment mechanism 1200 separated from a head shaft 1311 of the cutting head 1300. The head shaft 1311 is configured to penetrate through at least a portion of the body 1210 of the alignment mechanism 1200, as illustrated in FIG. 21. The illustrated head shaft 1311 has a rectangular cross-section and includes teeth 1314 on at least one side of the rectangular cross-section. The teeth 1314 are configured to interact with an engagement element 1220 that is essentially similar to the engagement element 220 described herein. Any other functional cross-section for a shaft may be used in other embodiments. The collar 1120 includes an opening 125 (FIG. 22) through which a connection element of the ankle clamp 400, such as a bracket 408 illustrated in FIG. 17, may be passed. In the illustrated embodiment, sliding of the collar 1120 of the guide base 1100 is regulated by pressing of the button 1409. Specifically, in this example when the button 409 is pressed, the collar 1120 is free to slide along the bracket 408, and when the button 409 is released, the collar 1120 is prevented from sliding along the bracket 408. Any other functional type of connection mechanism may be used in other embodiments, including for example and without limitation, a rack and pinion system, a setscrew, a threaded mechanism, worm gear system, or an automated drive system. Internal configuration and function of the alignment mechanism 1200 shown in FIGS. 21 and 22 is essentially similar in configuration and function to the alignment mechanism 200 described herein except that interaction of the engagement element 1220 is with the cutting head rather than with a portion of the guide base.

As shown in FIG. 21, the cutting head 1300 depicted is coupled to the alignment mechanism 1200. The cutting head 1300 illustrated in more detail in FIG. 22 includes a cutting head base 1320 configured to couple to the alignment mechanism 1200 and a removable mechanism 340 that is essential the same as the removable mechanism 340 as described herein, including the blade guide 360, the coupler 350, and the microadjustment element 370, along with their respective component parts. Operation of the microadjustment element 370 is independent from operation of the coupler 350 between the cutting head base 1320 and the removable mechanism 340. The illustrated cutting head 1300 is disclosed as a part of the tibial cutting guide 1001. However, in other embodiments, a cutting head within the scope of the disclosure herein may be an independently operating device or a component of another system that does not necessarily involve alignment for the resection of a tibia in preparation for an arthroplasty device.

Figure 23:
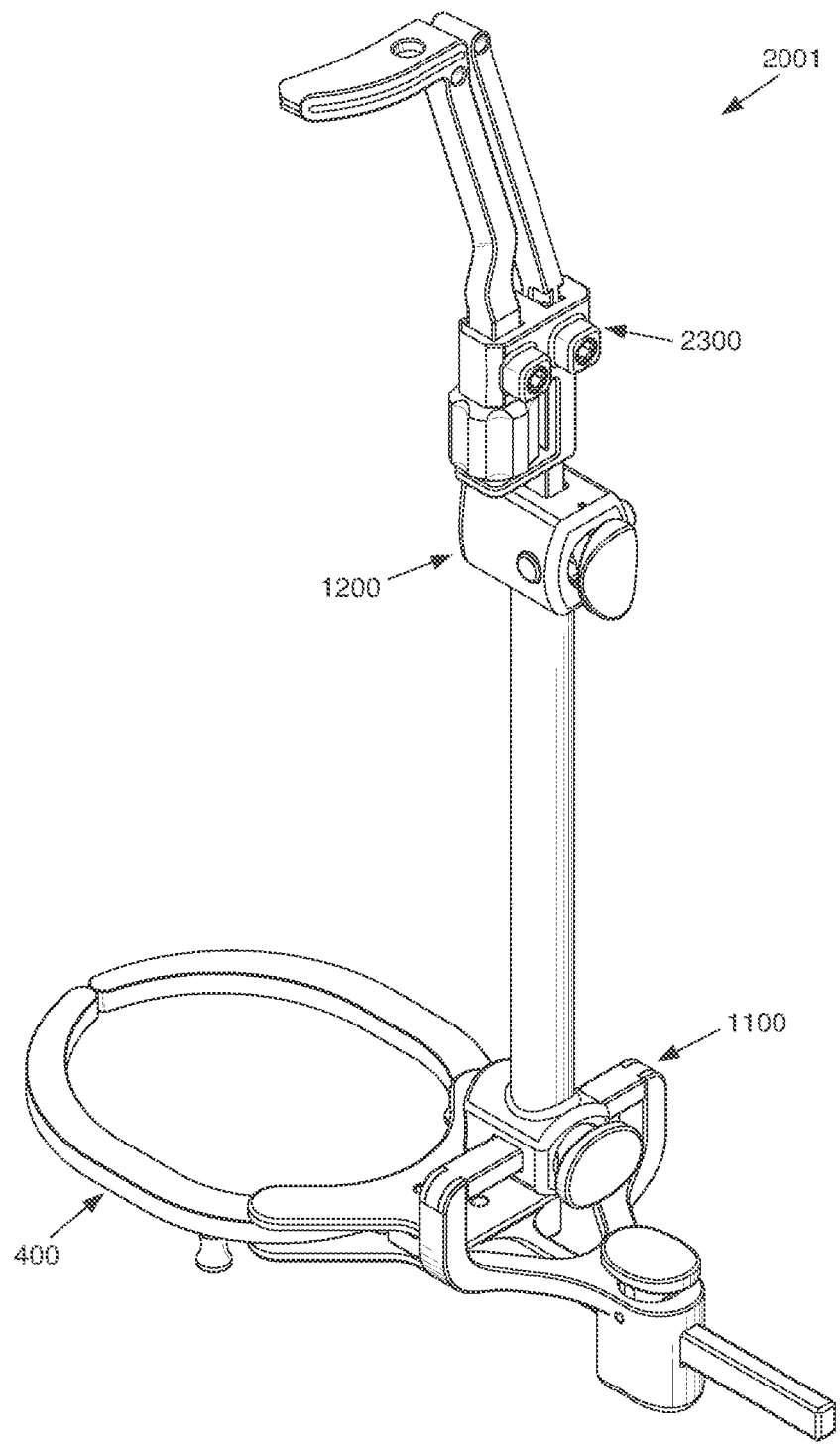
FIG. 23 is a perspective view of another embodiment of the cutting guide.
Figure 24:
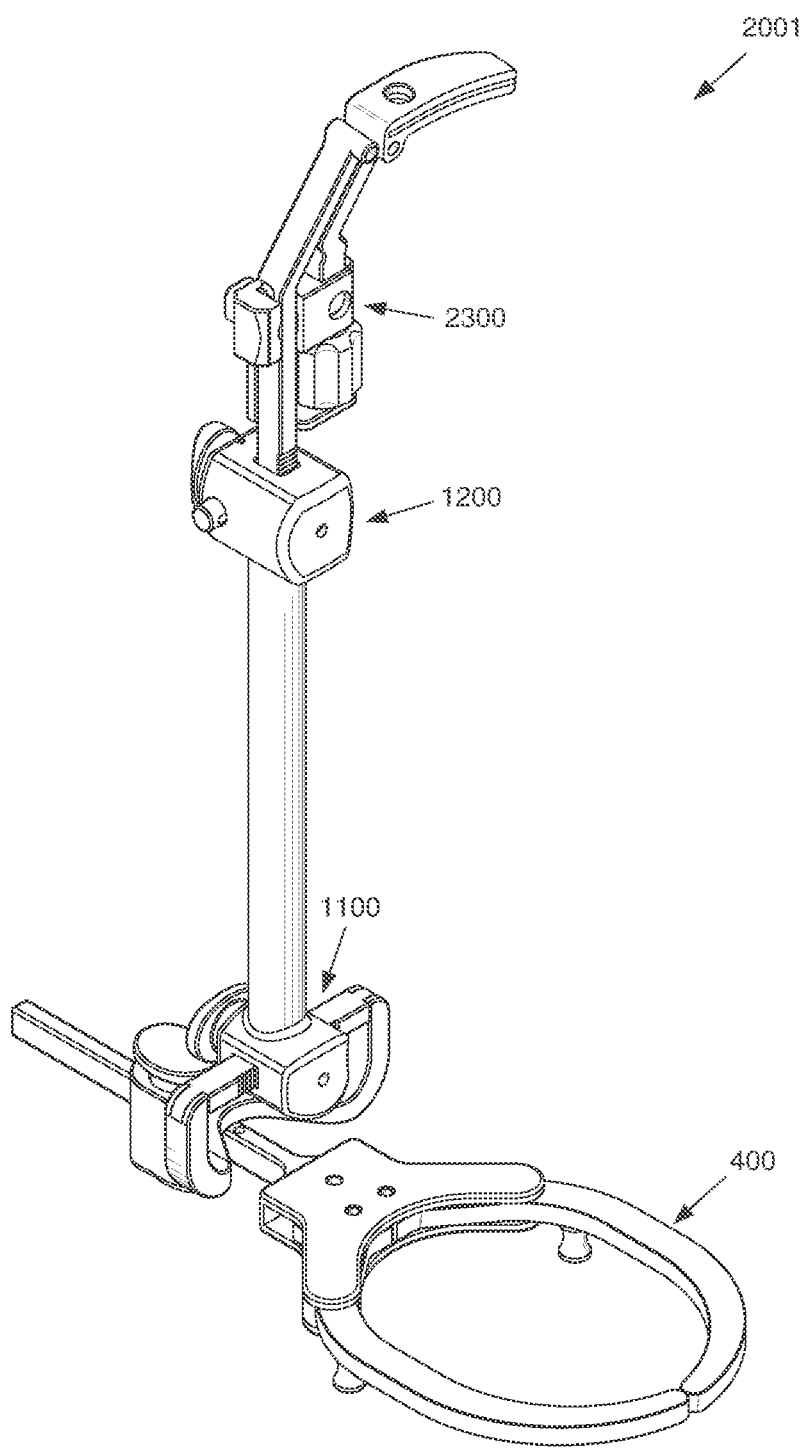
FIG. 24 is another perspective view of the embodiment of the cutting guide of FIG. 23.
Figure 25:
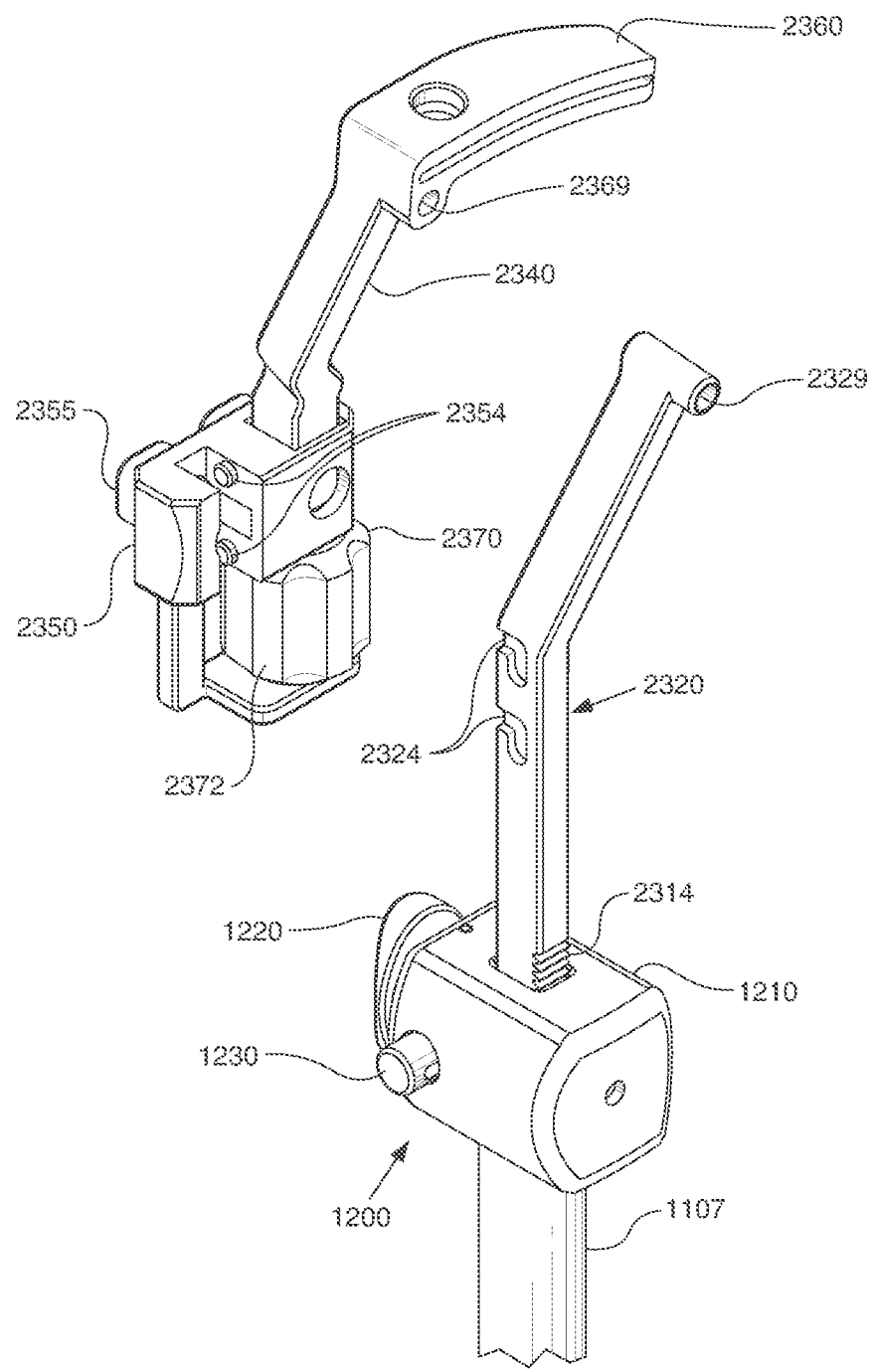
FIG. 25 is a partially exploded and enlarged perspective view of portions of the cutting guide of FIG. 24.
Figure 26:
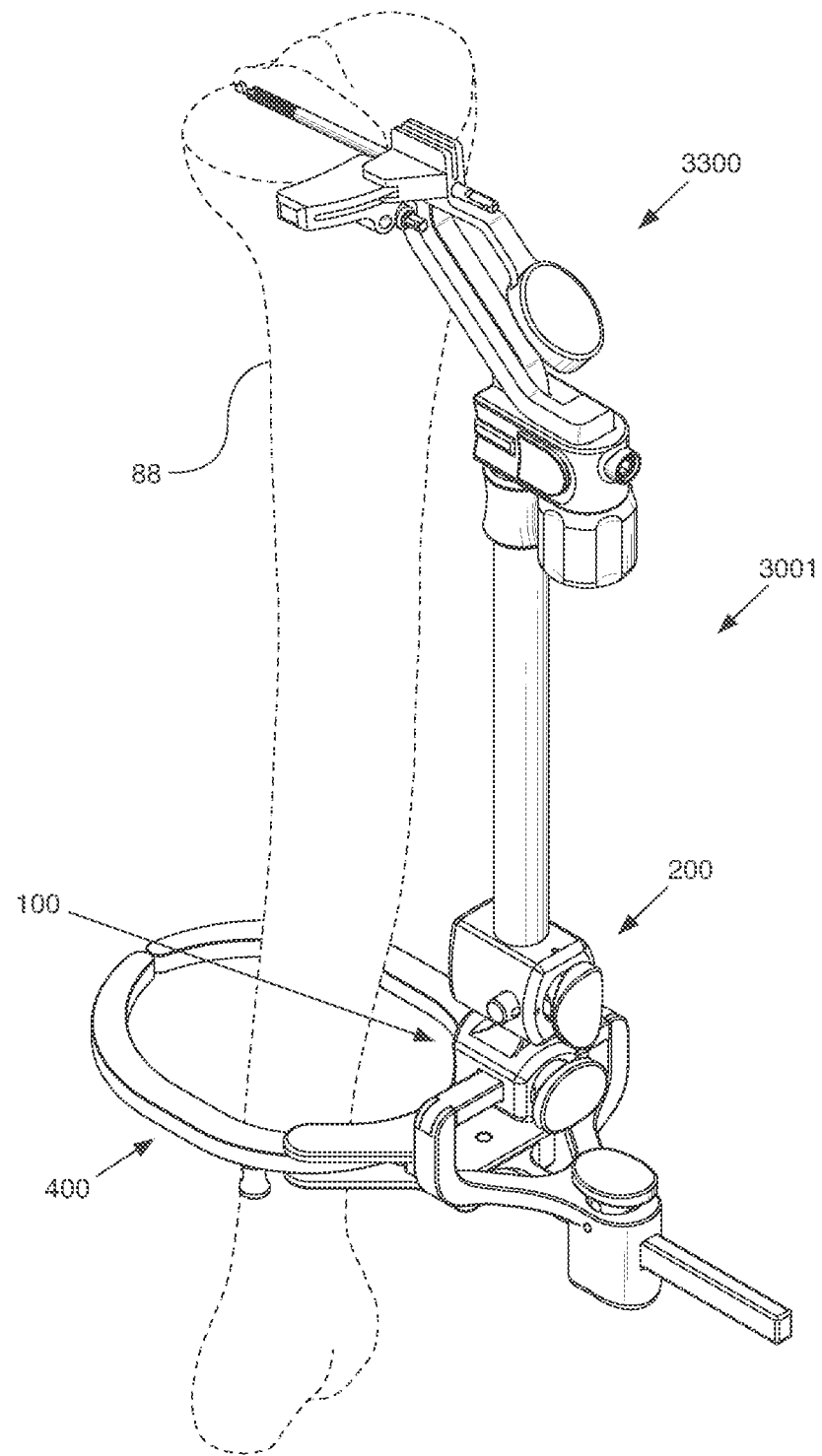
FIG. 26 is a perspective view of another embodiment of the cutting guide in position on a patient's tibia (patient's tibia drawn with phantom lines).
Figure 27:
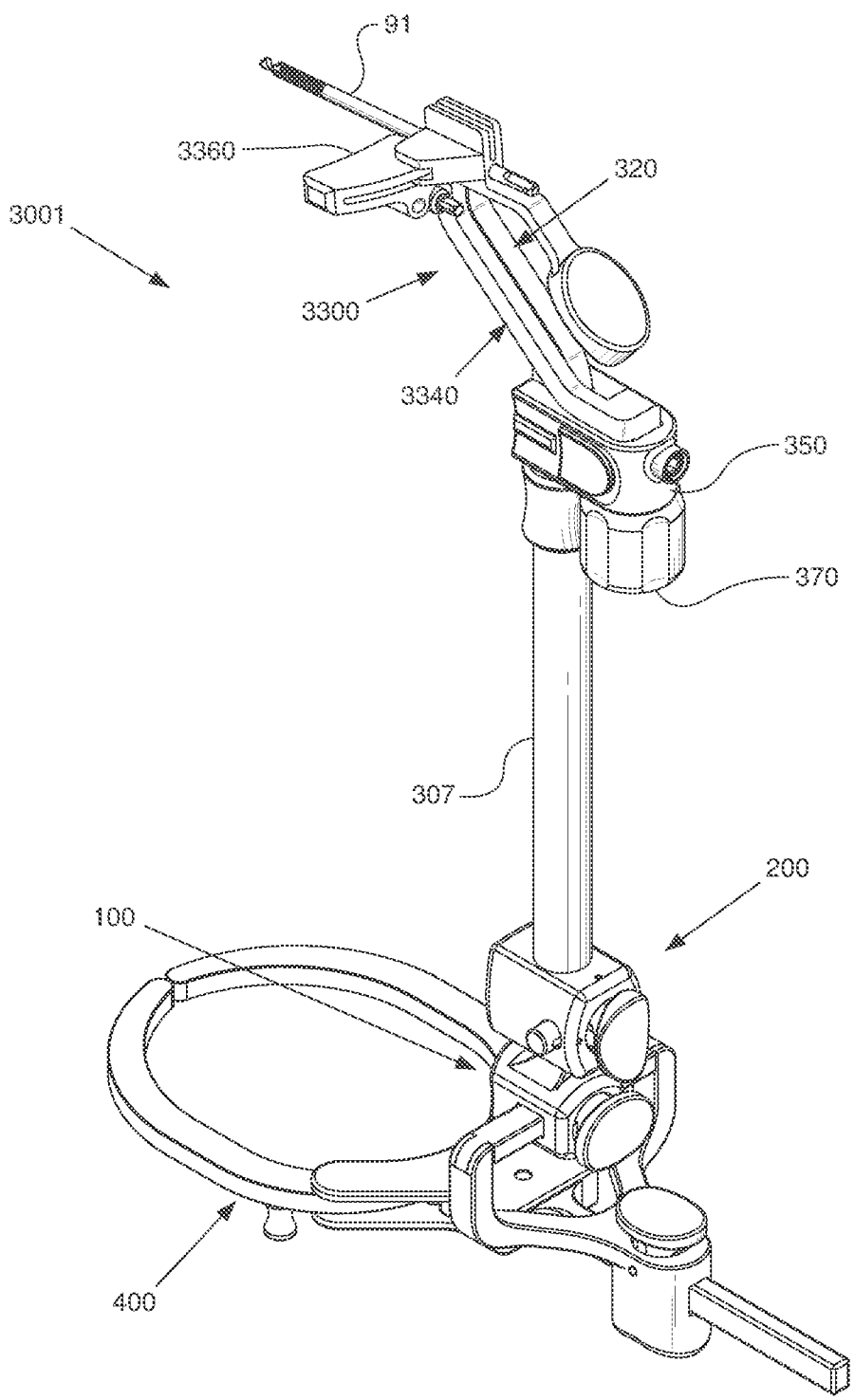
FIG. 27 is another perspective view of the embodiment of the cutting guide of FIG. 26.
Figure 28:
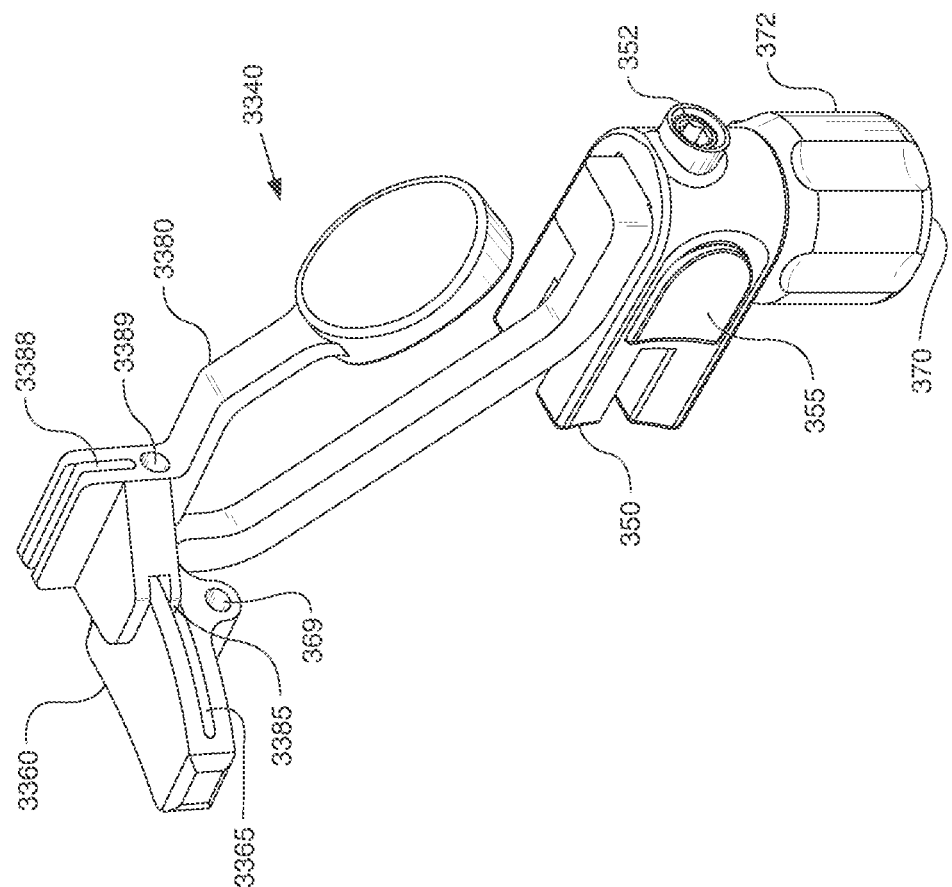
FIG. 28 is a perspective view of a removable mechanism of a cutting head of the cutting guide of FIG. 26.
Figure 29:
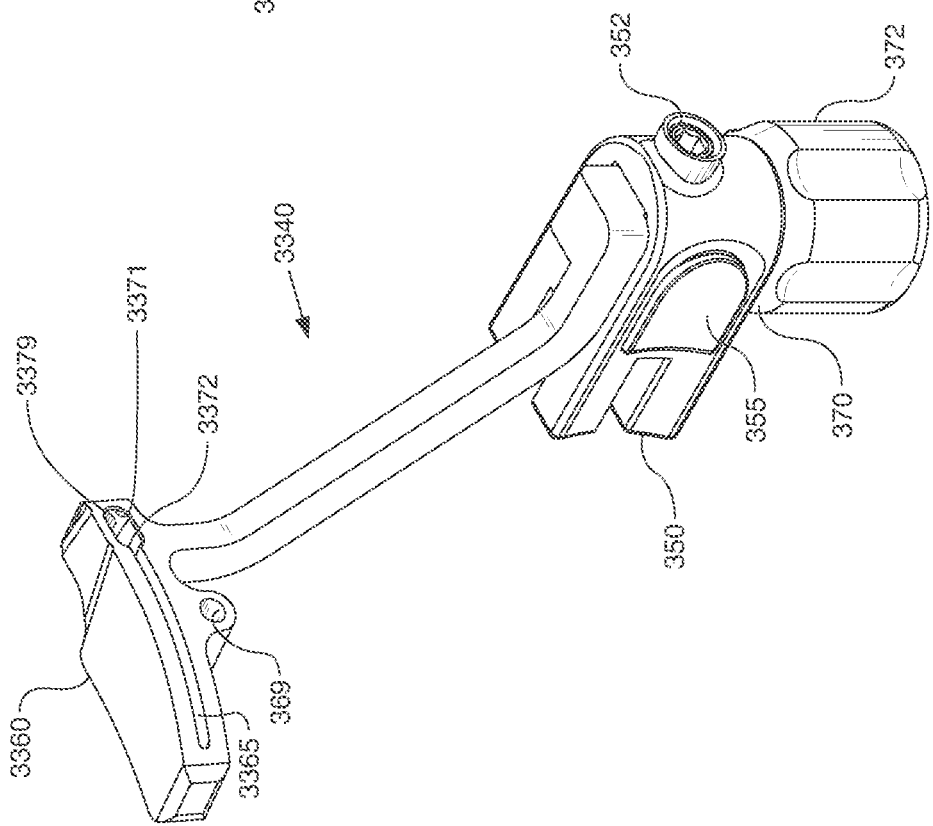
FIG. 29 is a perspective view of the removable mechanism of the cutting head with a modular capture device.

A tibial cutting guide 2001 is illustrated in FIGS. 23-25. The tibial cutting guide 2001 illustrated includes the guide base 1100, the alignment mechanism 1200, a cutting head 2300, and the ankle clamp 400. The alignment mechanism 1200 is movably coupled to the cutting head 1300 as described in association with the embodiment of FIGS. 21 and 22. However, the cutting head 2300 has a different configuration from the other embodiments.

The cutting head 2300 depicted is coupled to the guide base 1100 through the alignment mechanism 1200. The cutting head 2300 illustrated in more detail in FIG. 25 includes a cutting head base 2320 that is coupled to the alignment mechanism 1200 and includes a removable mechanism 2340 that includes a coupler 2350 releasably interconnectable with the cutting head base 2320 and configured to detach from the cutting head base 2320 upon activation. The coupler 2350 of the removable mechanism 2340 includes a push portion 2355 that disengages latch pins 2354 from pin connections 2324 on the cutting head base 2320. Disengaging the latch pins 2354 from the pin connections 2324 allows the removable mechanism 2340 to be separated from the cutting head base 2320, as illustrated in FIG. 25. Any other effective latch or capture mechanism may be used in embodiments of the invention. The embodiment of the cutting head base 2320 shown includes one pin hole 2329 for receiving a fastener by which the cutting head base 2320 may be coupled with the tibia. Different numbers of pin holes and pins may be used in other embodiments. The one or more fasteners may be pins, screws, staples, or any functional fastener device.

The removable mechanism 2340 shown also includes a blade guide 2360, and a microadjustment element 2370 connected to the coupler 2350 and coupled to the blade guide 2360. Embodiments of the blade guide may be adapted to direct a blade through only a portion of the tibia aligning with a single condyle landing area of the knee joint to facilitate preparation of a unicondylar knee implant. For example, a slot in the blade guide may limit the lateral travel or the angle of application of a blade capable of fitting through the blade guide, thereby directing the blade or only a portion of a tibia to which the device is been attached. The term "single condyle landing area" is intended to refer to the portion of a tibia to which a single condyle of a femur would substantially align when a knee is functioning properly. Other blade guides may be arranged, without limitation, to perform a total knee arthroplasty.

The microadjustment element 2370 of some embodiments is configured to move the blade guide 2360 to multiple positions relative to the coupler 2350. As shown in FIG. 25, the microadjustment element 2370 includes a knob 2372 and also includes a lift bolt and a retainer ring as described in association with other embodiments herein. The knob 2372 in the illustrated embodiment is configured to rotate freely and drive the lift bolt (and the blade guide 2360, to which the lift bolt is coupled) relative to the coupler 2350. By this operation the microadjustment element 2370 moves the blade guide 2360 substantially parallel with an axis moved by the alignment mechanism 1200 relative to the guide base 1100. The blade guide 360 may include indicia like the indicia 368 (FIGS. 12-15) on a lower portion of the blade guide 2360 near where the lift bolt is coupled that graphically represent the relative distance movements between the blade guide 2360 and the coupler 2350. When a desired position for the blade guide 2360 is obtained relative to the coupler 2350, a set screw or other lock may be tightened to fix the position of the blade guide 2360 relative to the coupler 2350. The blade guide 2360 also includes a pin hole 2369, and in other embodiments may include more than one, for receiving one or more fasteners by which the blade guide 2360 may be coupled with the tibia. The one or more fasteners may be pins, screws, staples, or any functional fastener device. Operation of the microadjustment element 2370 is independent from operation of the coupler 2350 between the cutting head base 2320 and the removable mechanism 2340.

The illustrated cutting head 2300 is disclosed as a part of the tibial cutting guide 2001. However, in other embodiments, a cutting head within the scope of the disclosure herein may be an independently operating device or a component of another system that does not necessarily involve alignment for the resection of a tibia in preparation for an arthroplasty device.

A tibial cutting guide 3001 is illustrated in FIGS. 26-32C. The tibial cutting guide 3001 illustrated includes the guide base 100, the alignment mechanism 200, a cutting head 3300, and the ankle clamp 400. The alignment mechanism 200 is movably coupled to the cutting head 3300 as described in association with the embodiment of FIG. 1. However, the cutting head 3300 has a different configuration from the other embodiments. The guide base 100, the alignment mechanism 200, and the ankle clamp 400 are essentially similar to the components described in association with the embodiment of FIG. 1.

The cutting head 3300 depicted is coupled to the alignment mechanism 200 through the tubular portion 307 of the cutting head 3300. The cutting head 3300 illustrated in more detail in FIGS. 27-32C includes a cutting head base 320 coupled to the alignment mechanism 200 and a removable mechanism 3340 that includes a coupler 350 releasably interconnectable with the cutting head base 320 and configured to detach from the cutting head base 320 upon activation. The coupler 350 of the removable mechanism 3340 includes a push portion 355 that disengages a latch from a connection on the cutting head base 320 (essentially similar to the progression from FIG. 14 to FIG. 15). The illustrated connection between the cutting head base 320 and the removable mechanism 3340 also includes rails on the cutting head base 320 that fit into a slot in the coupler 350. Disengaging the latch from the connection allows the removable mechanism 3340 to be separated from the cutting head base 320, as illustrated in FIGS. 28-30B, 31A, 31B, and 32A-32C. Any other effective latch or capture mechanism may be used in other embodiments of the invention. The embodiment of the cutting head base 320 shown includes two pin holes 329 (FIGS. 30C and 31C) for receiving one or more fasteners 99 by which the cutting head base 320 may be coupled with the tibia. The one or more fasteners 99 illustrated is a pin with shoulders, but may be other types of pins, screws, staples, or any functional fastener device.

The removable mechanism 3340 illustrated also includes a blade guide 3360, and a microadjustment element 370 connected to the coupler 350 and coupled to the blade guide 3360. Embodiments of the blade guide may be adapted to direct a blade through only a portion of the tibia aligning with a single condyle landing area of the knee joint to facilitate preparation of a unicondylar knee implant. For example, a slot in the blade guide may limit the lateral travel or the angle of application of a blade capable of fitting through the blade guide, thereby directing the blade to remove only a portion of a tibia to which the device is been attached. The term "single condyle landing area" is intended to refer to the portion of a tibia to which a single condyle of a femur would substantially align when a knee is functioning properly.

The slot in the body of the blade guide 3360 may also be described as an opening 3365 (FIGS. 28-31C) in the body sized and oriented to direct a blade. The opening 3365 in the body is sized and oriented to direct a blade by having a substantially close fit between a wider proportion side of the blade and the opening 3365. By a "close fit" it is intended to mean a fit that directs motion, but not a fit sufficiently tight to create potentially damaging or harmful friction between the blade's wider proportion sides and the opening 3365. The opening 3365 of the illustrated embodiment has a greater longitudinal direction and a lesser height substantially perpendicular to the longitudinal direction. Other blade guides may be arranged, without limitation, to perform a total knee arthroplasty. The blade guide 3360 also includes a pin slot 3379 in the body having a width in substantially the same direction as the longitudinal direction of the opening 3365 and a height less than the width.

The pin slot 3379 (FIGS. 28 and 30A-30C) is sized to have a substantially close fit between its height and an intersection pin 91 (FIGS. 27 and 30A-32C) configured to be inserted through the pin slot 3379 and a looser fit between its width and the intersection pin 91 such that the intersection pin 91 is able to be moved along the width of the pin slot 3379 and pivot about an axis parallel to the height of the pin slot 3379. In the illustrate embodiment (FIG. 28), both edges 3371, 3372 of the pin slot 3379 at the extents of the width of the pin slot 3379 are angled substantially away from perpendicular to the longitudinal direction of the opening 3365 in the body. In other embodiments, only one edge maybe angled substantially away from perpendicular, or in still other embodiments, both edges may be substantially perpendicular to the longitudinal direction of the opening 3365 in the body. In the illustrated embodiment, the pin slot 3379 is wider on the side of the blade guide 3360 configured to be positioned against a tibia than the pin slot 3379 is on the opposite side of the blade guide 3360. This configuration provides for a range of intersection pin 91 angling and medial-lateral positioning relative to the blade guide 3360, some of which are illustrated in FIGS. 32A-32C. The blade guide 3360 also includes a pin hole 369, and in other embodiments may include more than one, for receiving one or more fasteners by which the blade guide 3360 may be coupled with the tibia. The one or more fasteners may be pins, screws, staples, or any functional fastener device. Operation of the microadjustment element 370 is independent from operation of the coupler 350 between the cutting head base 320 and the removable mechanism 3340.

The embodiment of the device illustrated in FIGS. 26, 27, 29, and 31A-31C includes a modular capture device 3380 with a pin hole opening 3389 sized to have a substantially close fit to the intersection pin 91 configured to be inserted through the pin slot 3379 in the body of the blade guide 3360. The illustrated embodiment also includes a fin 3385 sized to engage in the opening 3365 in the body to provide orientation of the modular capture device 3380 relative to the body 3360. Some embodiments may not use a fin that fits in an opening in the body, but may instead rely on other landmarks or positioning devices for alignment. The modular capture device 3380 illustrated also includes an alignment slot 3388 in the modular capture device in which an alignment tool may be placed to orient the modular capture device 3380 relative to a patient's anatomy. For example and without limitation, an "Angel Wing" instrument may be used as an alignment tool by positioning the Angel Wing in the alignment slot at a proximal end of the Angel Wing and a distal end of the Angel Wing may be positioned at a specific landmark on the tibial plateau or distal femur. When the desired alignment is achieved, positioning for placement of an intersection pin 91 or other fixation device may be established or an intersection pin 91 may be inserted through the pin hole opening 3389 while holding the modular capture device 3380 in a fixed position relative to the blade guide 3360. The alignment slot 3388 may also be used to orient a sigitally directed saw blade to make a cut directly over the intersection pin 91. The alignment slot 3388 could be used as a direct guide of for a blade or a portion of a saw that is moving the saw blade may be configured to align in the alignment slot 3388 or a similarly situated slot.

The microadjustment element 370 of some embodiments is configured to move the blade guide 3360 to multiple positions relative to the coupler 350. The microadjustment element 370 with the knob 372 and their operation have been described in detail herein. Operating the microadjustment element 370 moves the blade guide 3360 substantially parallel with an axis moved by the alignment mechanism 200 relative to the guide base 100. When a desired position for the blade guide 3360 is obtained relative to the coupler 350, the set screw 352 may be tightened to fix the position of the blade guide 3360 relative to the coupler 350.

The illustrated cutting head 3300 is disclosed as a part of the tibial cutting guide 3001. However, in other embodiments, a cutting head within the scope of the disclosure herein may be an independently operating device or a component of another system that does not necessarily involve alignment for the resection of a tibia in preparation for an arthroplasty device.

Figure 17:
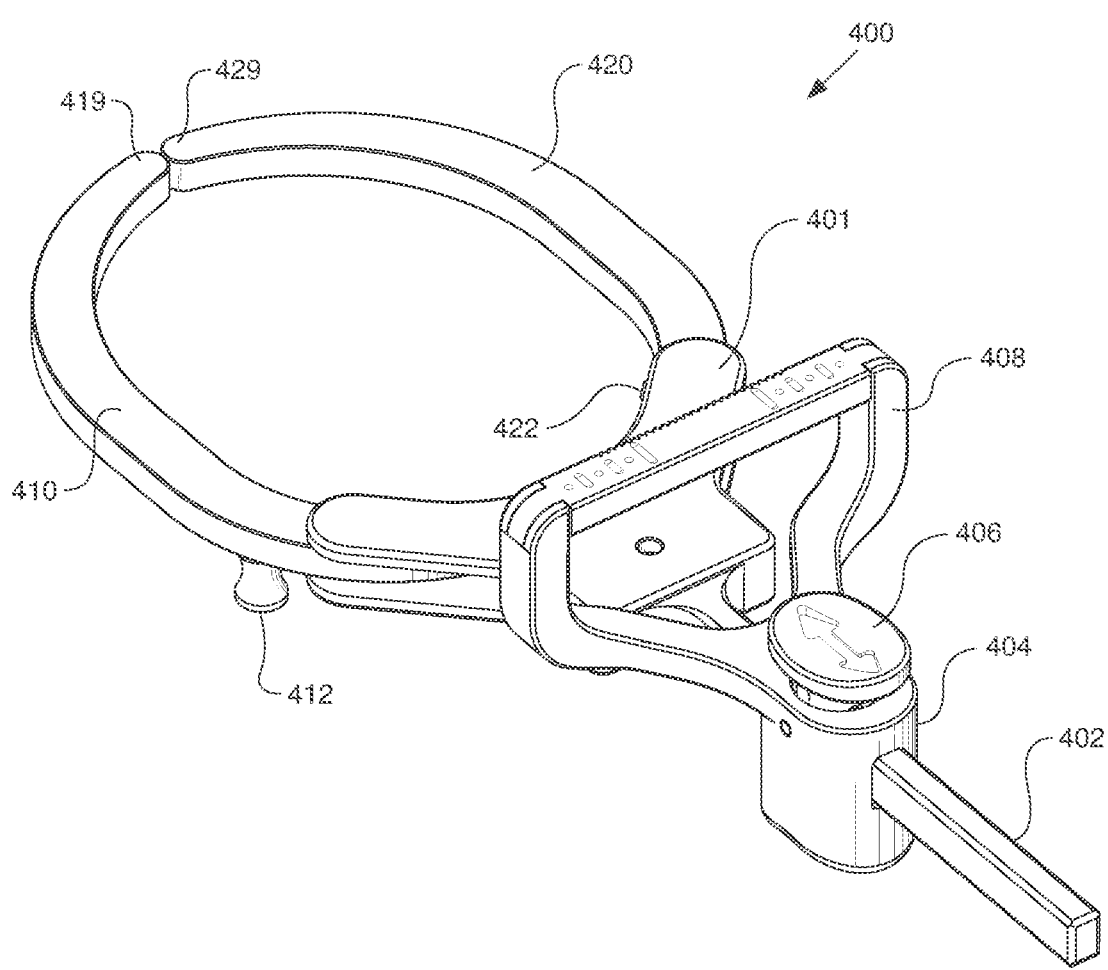
FIG. 17 is a perspective view of the ankle clamp of the cutting guide of FIG. 1 in a closed position.
Figure 18:
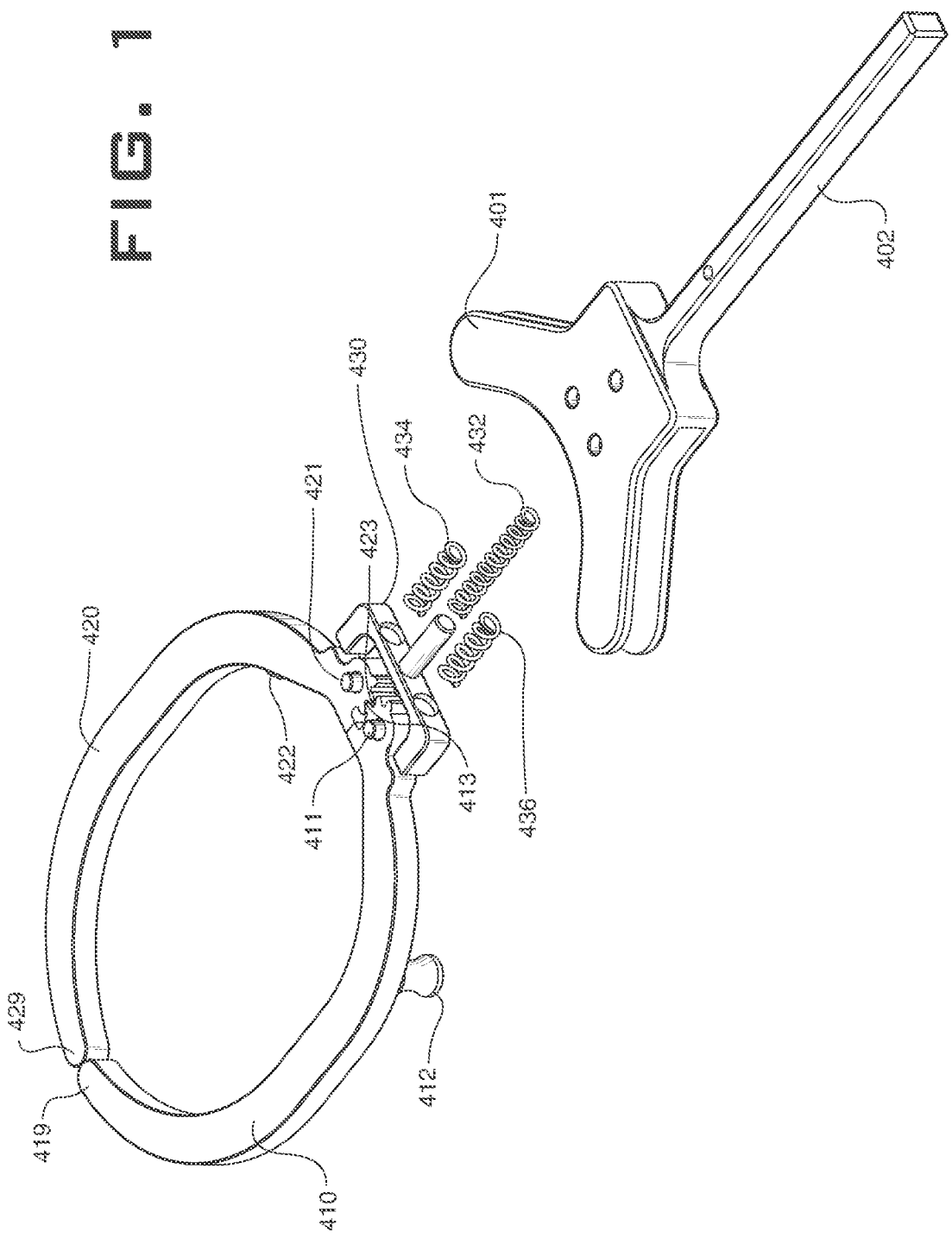
FIG. 18 is a partially exploded perspective view of a portion of the ankle clamp of FIG. 17 in a closed position.
Figure 19:
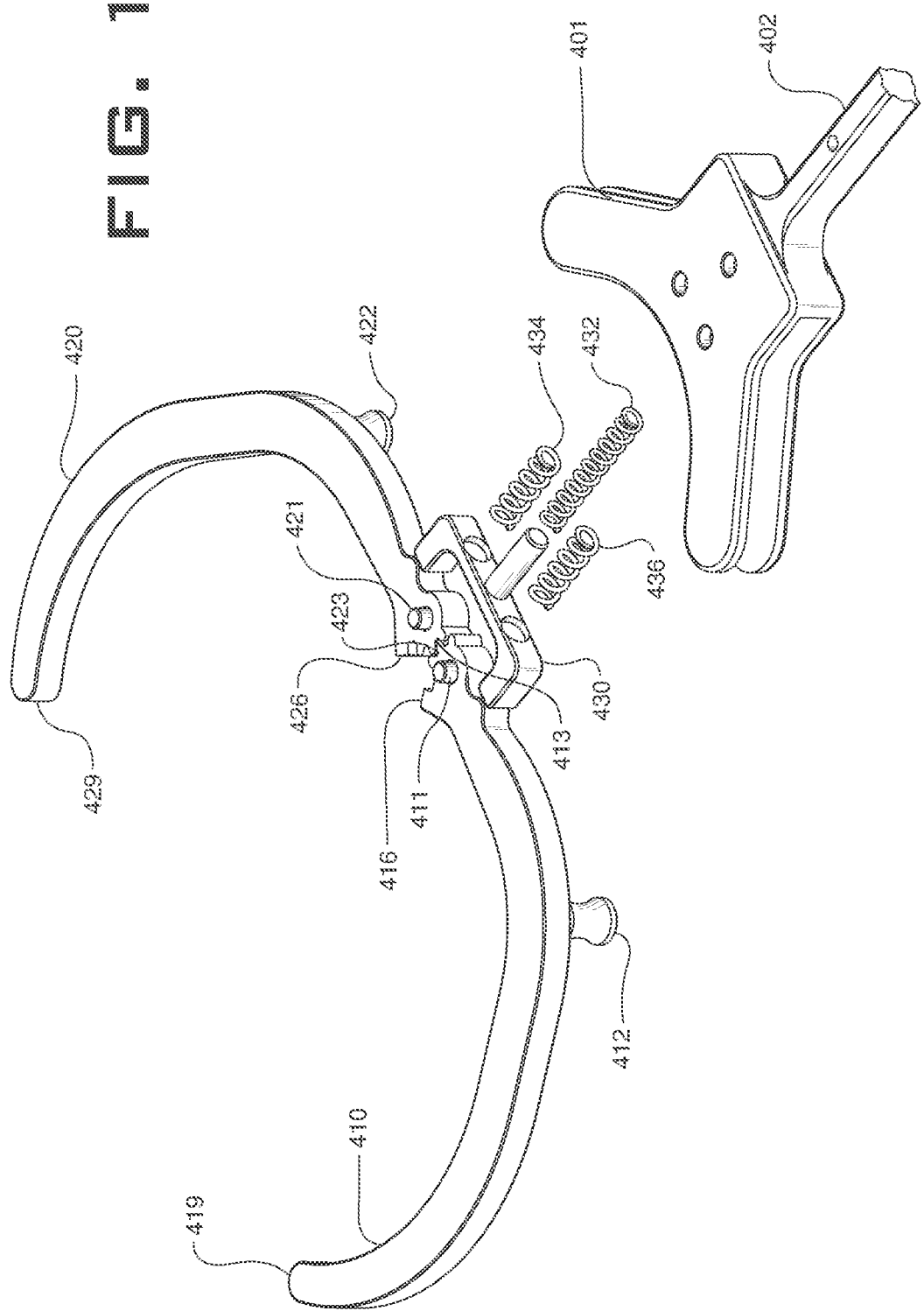
FIG. 19 is a partially exploded perspective view of a portion of the ankle clamp of FIG. 17 in an open position.
Figure 20:
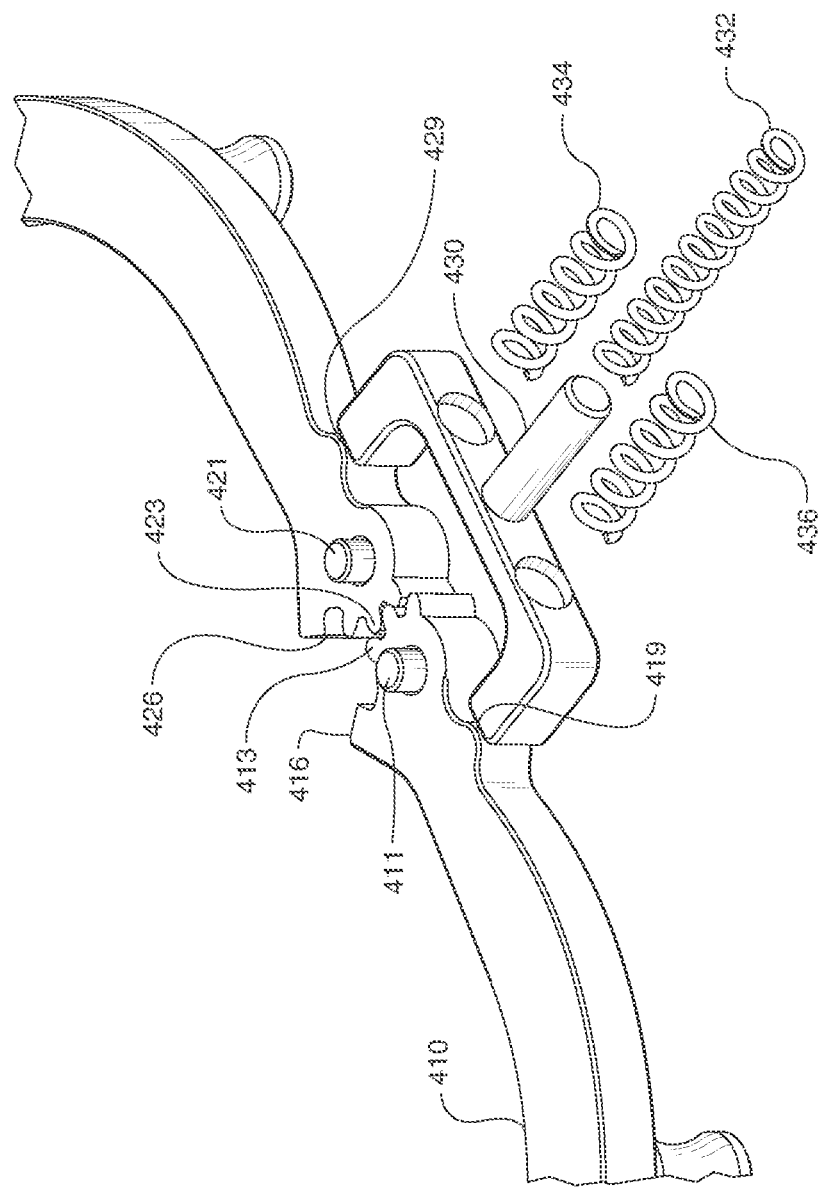
FIG. 20 is an enlarged view of part of the ankle clamp illustrated in FIG. 19.

An embodiment of the ankle clamp 400 is shown in FIGS. 1, 17-22, 23, and 24. In FIG. 1, for example, the ankle clamp 400 is coupled to the guide base 100. The illustrated embodiment of the ankle clamp 400 includes a housing 401, a first arm 410, and a second arm 420. The first arm 410 has a first pivot 411 and two or more first gear teeth 413 spaced along a radius from the first pivot 411, and a distal end 419. The first arm 410 is pivotally coupled to the housing 401 at the first pivot 411. The first arm 410 includes a first stop 416, as illustrated in FIGS. 19 and 20. The second arm 420 has a second pivot 421 and two or more second gear teeth 423 spaced along a radius from the second pivot 421. The second arm 420 has a distal end 429. The second arm 420 is pivotally coupled to the housing 401 at the second pivot 421, and has its two or more second gear teeth 423 interdigitating with the two or more first gear teeth 413 of the first arm 410. The gear teeth 413, 423 specifically illustrated are standard mechanical gear teeth, but in other embodiments may be any component or combination of components that interdigitate during motion of the arms 410, 420. For example and without limitation, the gear teeth may be thinner spikes or fingers, or may be larger scale bumps and divots or other shapes that cooperate between the arms or other intervening components. The second arm 420 includes a second stop 426 that contacts the first stop 416 of the first arm 410 when the first arm 410 and the second arm 420 are closed together. The ankle clamp 400 of the illustrated embodiment also includes an extension 402 that projects from the housing 401 and is configured to couple with an adjuster 404 that is coupled to the bracket 408 (FIG. 17). The extension 402 may be moved relative to the adjuster 404 and the bracket 408 when the button 406 is pressed. The extension 402 is fixed relative to the adjuster 404 and the bracket 408 when the button 406 is released. In other embodiments, the button 406 may be replaced by any other effective release and fixation device, or in some embodiments may be replaced with a fixed connection. The first arm 410 shown includes a first knob 412 that may be used by a user to grasp the first arm 410, or may be used to couple with first arm 410 in any effective manner. The second arm 420 shown includes a second knob 422 that may be used by a user to grasp the second arm 420, or may be used to couple with second arm 420 in any effective manner. The first pivot 411 and the second pivot 421 of the illustrated embodiment include pivot pins, but in other instances may include any effective device or capture capable of creating a fixed or floating pivot between one or both of the arms and the housing.

Embodiments of the ankle clamp may include a biasing element adapted to generate a biasing force to push a distal end of the first arm toward a distal end of the second arm. In the illustrated embodiment, the ankle clamp 400 includes biasing elements 432, 434, 436 that generate a biasing force to push distal end 419 of the first arm 410 toward distal end 429 of the second arm 420. The biasing elements 432, 434, 436 press against a biasing force interface bracket 430 between the biasing elements 432, 434, 436 and the first arm 410 and the second arm 420. This applies biasing force from the biasing elements 432, 434, 436 to the first arm 410 at a first point 419 (FIG. 20) on the first arm 410 away from the first pivot 411 and to applies biasing force from the biasing elements 432, 434, 436 to the second arm 420 at a second point 429 (FIG. 20) on the second arm 420 away from the second pivot 421. Other embodiments may include fewer or more biasing elements or biasing elements of different types. For example and without limitation, only the biasing element 432 may be used in some embodiments. The biasing elements 432, 434, 436 are helical springs, but different types of biasing elements (flat spring, coil springs, elastomeric materials, etc.) may be used in other embodiments. Biasing elements of differing lengths and with different spring constants may be used to create different force of closure and resistance profiles over the length of travel of the biasing elements, and consequently the arms 410, 420. The device disclosed includes the biasing force interface bracket 430, but other embodiments may omit a force distribution bracket such as this and apply biasing force directly from one or more biasing elements to the arms.

The illustrated ankle clamp 400 is disclosed as a part of the tibial cutting guides 1, 1001, and 2001. However, in other embodiments, a clamping device within the scope of the disclosure herein may be an independently operating device or a component of another system that does not necessarily involve alignment for the resection of a tibia in preparation for an arthroplasty device.

An embodiment of the invention is a method of positioning a cutting guide, such as the cutting guide 1, 1001, 2001, 3001 and resecting a patient's tibia. Such a method may include moving a mode selector like the mode selector 230, 1230 to a position that allows free length movement of the cutting guide 1 (FIGS. 8-9). In this example, the position of the mode selector 230 where free length movement is not allowed is the position illustrated in FIGS. 3 and 5. The position where free length movement is permitted is the position of the mode selector illustrated in FIGS. 8-9. The method may also include opening two arms 410, 420 of a clamp 400 away from a center of the clamp 400 by moving one of the arms away from the center of the clamp 400 and placing the clamp 400 on the patient's ankle. The method may include closing the two arms 410, 420 of the clamp 400 by moving one of the arms toward the center of the clamp 400. A length of the cutting guide 1, 1001, 2001, 3001 may be adjusted to place an at least two piece cutting head 300, 1300, 2300, 3300 of the cutting guide 1, 1001, 2001, 3001 adjacent to the tibia. Adjusting the length of the cutting guide 1, 1001, 2001 to place an at least two piece cutting head 300, 1300, 2300, 3300 of the cutting guide 1, 1001, 2001, 3001 adjacent to the tibia may include pulling or pushing ends of the cutting guide 1, 1001, 2001, 3001 apart or together while the cutting guide 1, 1001, 2001, 3001 is in the free length movement state describe herein.

The method may also include returning the mode selector 230, 1230 to a position that does not allow free length movement to set the cutting guide 1, 1001, 2001, 3001 length (FIGS. 3 and 5). A first portion (in this example, the cutting head base 320, 1320, 2320) of the cutting head 300, 1300, 2300, 3300 may be attached to the tibia and the tibia may be cut through a second portion (in this example, the removable mechanism 340, 2340, 3340, and in particular the blade guide 360, 2360, 3360) of the cutting head 300, 1300, 2300, 3300 that is adjustable relative to the first portion of the cutting head and removable relative to the first portion of the cutting head. For example, the act of attaching a first portion of the cutting head to the tibia may include inserting one or more fasteners through one or more pin holes 329, 2329 in the first portion of the cutting head (the cutting head base 320, 1320, 2320 here) and into the tibia. In some embodiments, the act of cutting the tibia through a second portion of the cutting head, such as the blade guide 360, 2360, 3360 may include cutting only a single condyle landing area of a knee joint to facilitate preparation for a unicondylar knee implant. Cutting only a single condyle landing area may be directed by control of a blade by the second portion of the cutting head. For example, if the size and shape of the blade are coordinated with the size and shape of the opening in the blade guide 360, 2360, 3360 then it is possible to only allow a blade to extend a certain distance and direction from the blade guide 360, 2360, 3360. Other blade guides may be arranged, without limitation, to perform a total knee arthroplasty. A second portion of the cutting head, such as the blade guide 360, 2360, 3360, may be attached to the tibia by inserting one or more fasteners through one or more pin holes 369, 2369 (FIGS. 10, 13, 16, 25, and 28-31C) in the second portion of the cutting head 320, 1320, 2320 and into the tibia.

Optionally, for example if believed to be advantageous by a user, method embodiments may include removing the second portion of the cutting head relative to the first portion of the cutting head to better visualize the tibia. If an additional cutting of the tibia is deemed useful, the second portion of the cutting head may be replaced onto the first portion of the cutting head, adjustment of the second portion of the cutting head relative to the first portion of the cutting head may be made, and cutting the tibia through the second portion of the cutting head may be accomplished. In the illustrated embodiment, this would include removing the removable mechanism 340, 2340, 3340 relative to the cutting head base 320, 1320, 2320 to better visualize the tibia. If an additional cutting of the tibia is deemed useful, the removable mechanism 340, 2340, 3340 may be replaced onto the cutting head base 320, 1320, 2320. Adjustment of the removable mechanism 340, 2340, 3340 relative to the cutting head base 320, 1320, 2320 may be made using the microadjustment element 370, 2370, and cutting of the tibia through the blade guide 360, 2360, 3360 of the cutting head 300, 1300, 2300, 3300 may be accomplished. In the illustrated embodiment, replacing the second portion of the cutting head onto the first portion of the cutting head returns the second portion of the cutting head to substantially the same location relative to the tibia. Such functionality is described in association with the operation of the push portion 355, 2355 that disengages and reengages the latch 354, 2354 from the connection 324, 2324 on the cutting head base 320, 1320, 2320 in association with the progression from FIG. 14 to FIG. 15.

An example method of length adjustment of a cutting guide, such as the cutting guide 1, 1001, 2001, 3001 with an alignment mechanism, such as the alignment mechanism 200, 1200 is configured to function in three operating conditions. The method may include locating a mode selector, such as the mode selector 230, 1230, in a location defining a first state that permits two operating conditions. Such a location is defined by the location of the mode selector 230 illustrated in FIGS. 3 and 5-7. In this location, the two possible operating conditions are a condition where force is not being applied to an engagement element of the alignment mechanism 200, 1200 by a user and the engagement element 220, 1220 is in contact with a portion of another component, like the shaft 110 in FIGS. 3 and 5; and a condition where force is being applied to the engagement element 220, 1220 by a user and the engagement element 220, 1220 is not in contact with a portion of another component, like the shaft 110 in FIGS. 6-7. In this second condition, length adjustment of the cutting guide is accomplished by pulling or pushing ends of the cutting guide 1, 1001, 2001, 3001 apart or together while force is being applied to the engagement element 220, 1220 by a user.

This example method may also include locating the mode selector 230, 1230 in a location defining a second state that permits an operating condition (see FIGS. 8 and 9) defined as a condition where regardless of whether force is being applied to the engagement element 220 by a user, the engagement element 220 is not in contact with a portion of another component, and wherein in this condition length adjustment of the cutting guide is accomplished by pulling or pushing ends of the cutting guide 1, 1001, 2001, 3001 apart or together.

Another method of the invention includes positioning a two-part cutting head having a cutting head base and a removable mechanism relative to a bone or other tissue to be resected. In the illustrated embodiment positioning is positioning of a two-part cutting head relative to a tibia. The method may include coupling the cutting head base 320, 1320, 2320 to the tibia. For example, coupling the cutting head base 320, 1320, 2320 may be accomplished by passing one or more fasteners through one or more holes 329, 2329 in the cutting head base 320, 1320, 2320 and into the tibia.

For this method, a user such as a surgeon has the option of choosing to alter the position of the removable mechanism 340, 2340, 3340 relative to the cutting head base 320, 1320, 2320 if a blade guide 360, 2360, 3360 of the removable mechanism 340, 2340, 3340 is not in a desired location relative to the tibia by altering a microadjustment element 370, 2370. For example, the knob 372, 2372 may be turned to drive the lift bolt 374 (and the blade guide 360, 2360, 3360, to which the lift bolt 374 is coupled) relative to the coupler 350, 2350, which is attached to the cutting head base 320, 1320, 2320. Some method embodiments such as this one include optionally, detaching the removable mechanism 340, 2340, 3340 from the cutting head base 320, 1320, 2320, as illustrated in FIGS. 10, 16, 22, 25, 28-30B 31A, 31B, and 32A-32C, to better visualize the tibia behind the removable mechanism 340, 2340, 3340. Some methods may additionally include, optionally, returning the removable mechanism 340, 2340, 3340 to the cutting head base 320, 1320, 2320. When returned to the cutting head base 320, 1320, 2320, the blade guide 360, 2360, 3360 of the removable mechanism 340, 2340, 3340 is in substantially the same location as when detached from the cutting head base 320, 1320, 2320 due to the operation of the coupler 350, 2350, as described in association with the operation of the push portion 355, 2355 that disengages and reengages the latch 354, 2354 from the connection 324, 2324 on the cutting head base 320, 1320, 2320 (see FIGS. 14 and 15).

A method of operating an ankle clamp is also disclosed. The method may include operating a cutting guide, such as the cutting guide 1, 1001, 2001, 3001 that includes an ankle clamp 400 with a housing such as the housing 401. The example ankle clamp 400 includes a first arm 410 and a second arm 420. Method acts may include moving the first arm 410 with a first pivot 411 and two or more gear teeth 413 spaced along a radius from the first pivot 411. The first arm 410 illustrated is pivotally coupled to the housing 401 at the first pivot 411, away from a center of the ankle clamp 400. Movement of the first arm 410 away from the center of the ankle clamp 400 about the first pivot 411 causes the second arm 420 that has a second pivot 421 and two or more gear teeth 423 spaced along a radius from the second pivot 421, the second arm 420 being pivotally coupled to the housing 401 at the second pivot 421, and having its two or more gear teeth 423 interdigitating with the two or more gear teeth 413 of the first arm 410 to also move away from a center of the ankle clamp 400 while pivoting about the second pivot 421.

In some embodiments, such as the illustrated embodiment, moving the first arm 410 away from the center of the ankle clamp 400 about the first pivot 411 compresses biasing elements 432, 434, 436 against the housing 401. In this case, moving the first arm 410 away from the center of the ankle clamp 400 about the first pivot 411 moves the first arm 410 and the second arm 420 against a biasing force interface bracket 430 that compresses biasing elements 432, 434, 436 against the housing 401.

Figure 30C:
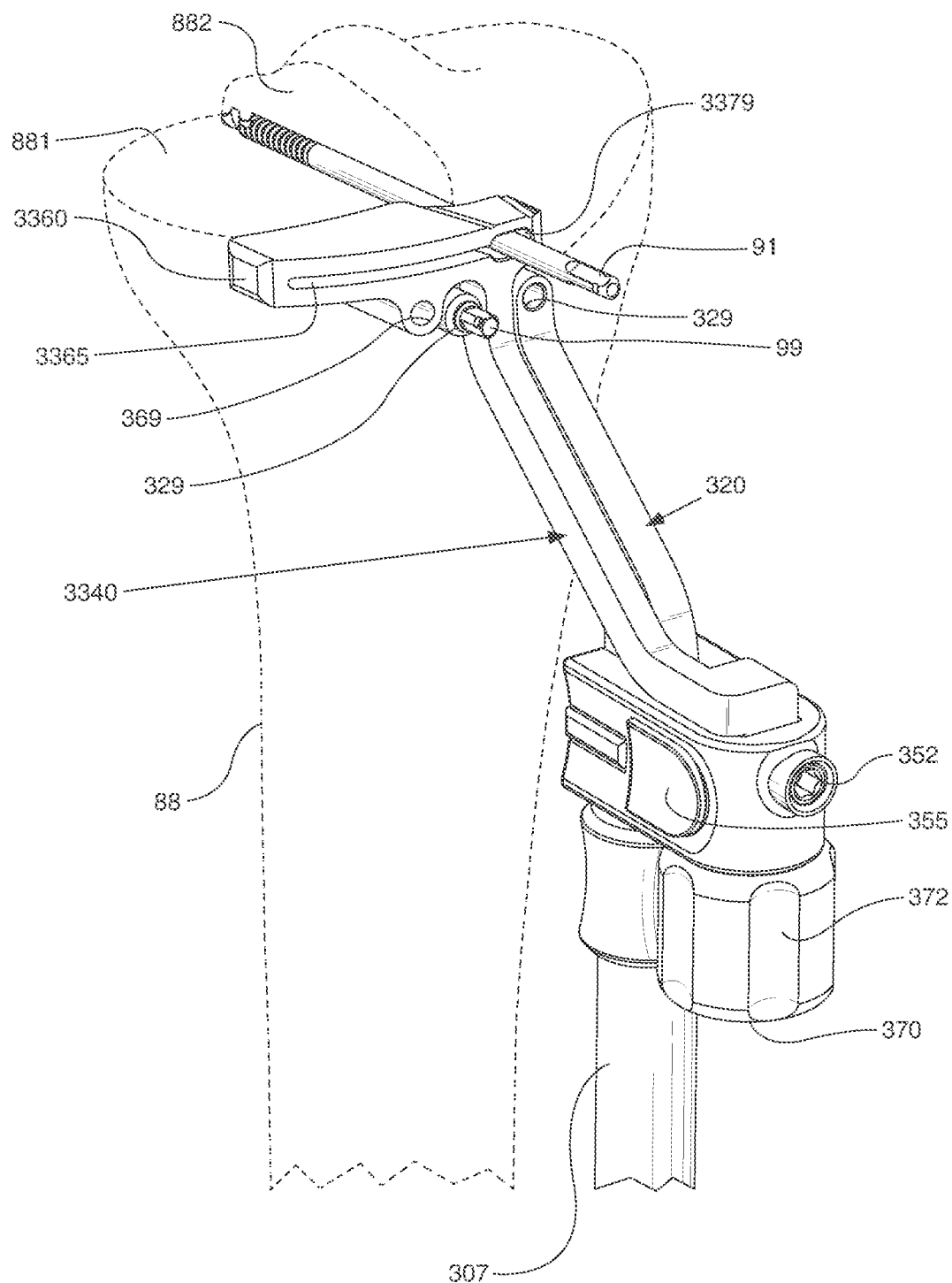
FIG. 30C is a perspective view of the removable mechanism of the cutting head with the intersection pin shown in FIG. 30A and a fixation pin, both the intersection pin and the fixation pin being coupled to a tibia that has been prepared to receive a unicondylar implant.
Figure 31C:
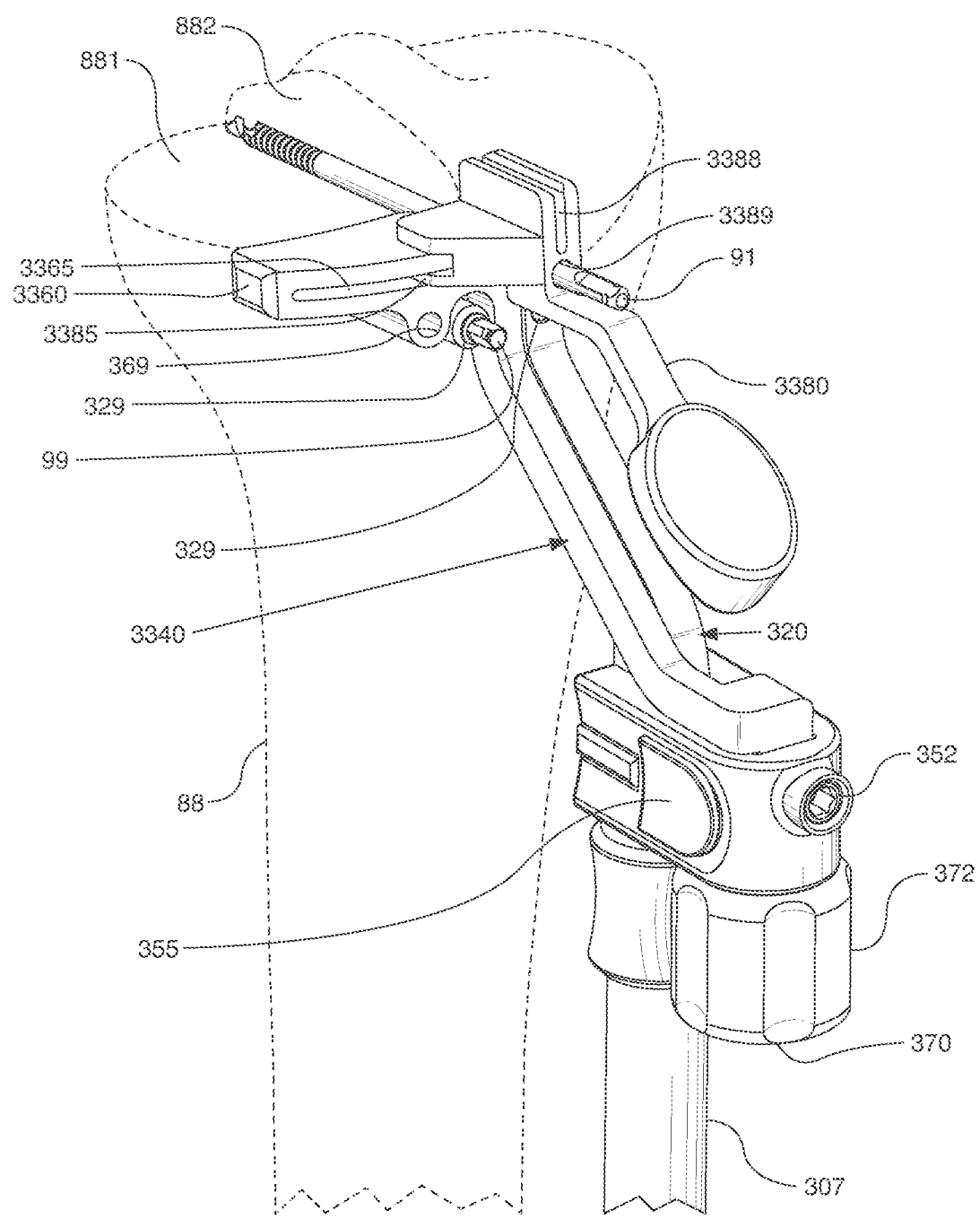
FIG. 31C is a perspective view of the removable mechanism of the cutting head with the intersection pin and the modular capture device shown in FIG. 31A with a fixation pin, both the intersection pin and the fixation pin being coupled to a tibia that has been prepared to receive a unicondylar implant.

Another embodiment of the invention is a method of positioning a cutting guide 3001 and resecting a patient's tibia 88 in preparation for placing a unicondylar tibial implant. The method will be described primarily in association with FIGS. 26-32C, but note that other cutting guides described herein (1, 1001, 2001), and still other cutting guides, may be used to perform some or all of the acts detailed in association with this method embodiment. The method embodiment may include attaching a clamp of a cutting guide at or near the patient's ankle. For example, the clamp 400 is shown in position near the patient's ankle in FIG. 26. Any other effective clamping or coupling, including temporary attachment with a fastener, may be accomplished to achieve attachment within the meaning intended for this method. Another act of the method embodiment includes adjusting the cutting guide 3001 to position a cutting head 3300 with a blade guide 3360 to align the blade guide 3360 to a location where a transverse cut in the patient's tibia can be made through the blade guide 3360. Adjustment of the cutting guide 3001 may be accomplished by operation of all or some of the controls described in association with the guide base 100, alignment mechanism 200, and cutting head 3300. The method may also include attaching a portion of the cutting head 3300 to the patient's tibia 88. For example, one or more fasteners 99 may be inserted through the pin holes 329, as is shown in FIGS. 30C and 31C. This act of attaching a portion of the cutting head 33000 to the patient's tibia 88 may include driving a headed pin into the tibia 88, as is illustrated with the one or more fasteners 99 shown in FIGS. 30C and 31C.

The present method may also include identifying relative to the cutting head 3300 an angle of insertion and a medial-lateral location for an intersection pin 91 that is to be placed through the pin slot 3371 in the blade guide 3360, where the intersection pin 91 is to be placed along a trajectory that defines an extent of a transverse cut to be made in the tibia 88 where the transverse cut is to intersect with a sagittal cut to be made in the tibia 88. Example cuts are illustrated in FIGS. 30C and 31C as a transverse cut 881 and a sagittal cut 882 that meet along a line defined by the intersection pin 91. The method described therefore also includes placing the intersection pin 91 in the tibia 88 through the pin slot 3379 in the blade guide 3360 at the identified angle, making the sagittal cut 882 using the intersection pin 91 as a stop, and making the transverse cut 881 through the blade guide 3360 using the intersection pin 91 as a stop. Identification of different angles for the intersection pin 91 relative to the blade guide 3360 are depicted in FIGS. 32A-32C. Note that the intersection pin 91 can be moved both in a medial-lateral direction and at an angle relative to the blade guide 3360 to accomplish intersection pin 91 placement along a desired trajectory even after the blade guide 3360 is fixed relative to the tibia 88.

The act of making the sagittal cut 882 may include placing a modular capture device 3380 in engagement with the blade guide 3360 as shown in FIGS. 26, 27, 29, and 31A-31C. In the embodiment illustrated, but not necessarily in all embodiments, engaging the modular capture device 3380 with the blade guide 3360 includes placing a fin 3385 of the modular capture device 3380 sized to engage with the blade guide 3360 in the opening 3365 of the blade guide 3360. In other embodiments, a modular capture device may not include a fin that engages with the blade guide, but may instead rely on other landmarks or positioning devices for alignment. The modular capture device 3380 illustrated includes a pin opening 3389 oriented along the trajectory that defines an extent of the transverse cut 881 to be made in the tibia 88 where the transverse cut 881 is to intersect with the sagittal cut 882 to be made. The pin opening 3389 illustrated is sized to have a substantially close fit to the intersection pin 91 configured to be inserted through the pin slot. In some method embodiments, the sagittal cut 882 is made with the aid of an alignment slot 3388 in the modular capture device 3380, where the alignment slot 3388 is substantially parallel with the pin opening 3389 in the modular capture device 3380. The intersection pin 91 shown is used as a stop for the sagittal cut 882. The alignment slot 3388 may be used as an aid by placing an "Angel Wing" instrument in the alignment slot 3388 with a proximal end of the Angel Wing in the alignment slot 3388 while a distal end of the Angel Wing is positioned at a specific landmark on the tibial plateau or distal femur. When the desired alignment is achieved, positioning for placement of an intersection pin 91 or other fixation device along a desired trajectory may be established or an intersection pin 91 may be inserted through the pin hole opening 3389 while holding the modular capture device 3380 in a fixed position relative to the blade guide 3360. The desired trajectory may be the trajectory that defines an extent of the transverse cut 881 to be made in the tibia 88, where the transverse cut 881 is to intersect with the sagittal cut 882 to be made.

In some embodiments, the modular capture device 3380 is moved over the intersection pin 91 after the intersection pin 91 has been placed in the tibia 88, and thereafter the modular capture device 3380 is engaged with the blade guide 3360 to stabilize the modular capture device 3380 relative to the blade guide 3360. In some embodiments, the transverse cut 881 is made after the modular capture device 3380 is removed from the blade guide 3360.

Various embodiments of an instrument set in whole or its components individually may be made from any biocompatible material. For example and without limitation, biocompatible materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys.

Terms such as proximal, distal, lateral, width, height, length, against, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

Embodiments of the invention may include claims to:
1. A tibial cutting guide comprising:
   a guide base;
   a cutting head comprising:
      a cutting head base, and
      a removable mechanism that includes at least:
         a coupler releasably interconnectable with the cutting head base and configured to detach from the cutting head base upon activation,
         a blade guide, and
         a microadjustment element connected to the coupler and coupled to the blade guide, the microadjustment element being configured to move the blade guide to multiple positions relative to the coupler,
         wherein operation of the microadjustment element is independent from operation of the coupler between the cutting head base and the removable mechanism; an
   alignment mechanism coupled between the guide base and the cutting head comprising:
      a body that couples with the guide base and the cutting head base,
      an engagement element movable relative to the body to selectively restrict or permit movement of the guide base relative to the cutting head base, and
      a mode selector configured to allow the engagement element to be selectively engaged and disengaged to restrict or permit movement of the guide base relative to the cutting head base when the mode selector is in a first state and configured to apply a force to the engagement element to urge the engagement element to continuously permit movement of the guide base relative to the cutting head base in a second state; and an ankle clamp coupled to the guide base comprising: a housing, a first arm with a first pivot and two or more first gear teeth spaced along a radius from the first pivot, the first arm being pivotally coupled to the housing at the first pivot, and a second arm with a second pivot and two or more second gear teeth spaced along a radius from the second pivot, the second arm being pivotally coupled to the housing at the second pivot, and having its two or more second gear teeth interdigitating with the two or more first gear teeth of the first arm.

2. The tibial cutting guide of claim 1 wherein the guide base includes at least a shaft and a collar, the shaft configured to penetrate through at least a portion of the alignment mechanism and the collar including an opening through which a connection element for the ankle clamp may be passed.

3. The tibial cutting guide of claim 2 wherein the shaft has a rectangular cross-section and includes teeth on at least one side of the rectangular cross-section configured to interact with the engagement element of the alignment mechanism.

4. The tibial cutting guide of claim 1 wherein a portion of the body of the alignment mechanism is tubular.

5. The tibial cutting guide of claim 1 wherein the engagement element includes teeth configured to engage with the guide base to restrict movement of the body relative to the guide base.

6. The tibial cutting guide of claim 1 wherein the engagement element includes a first opening configured to receive a portion of the guide base.

7. The tibial cutting guide of claim 6 wherein the engagement element includes a second opening configured to receive the mode selector.

8. The tibial cutting guide of claim 1 wherein the engagement element includes a first opening configured to receive a portion of the cutting head.

9. The tibial cutting guide of claim 8 wherein the engagement element includes a second opening configured to receive the mode selector.

10. The tibial cutting guide of claim 1 wherein the mode selector is configured to fit through the engagement element to interact with an interior portion of the engagement element.

11. The tibial cutting guide of claim 1 wherein the mode selector has cylindrical cross-sections of varying diameters along its length.

12. The tibial cutting guide of claim 1 wherein the mode selector includes a smaller diameter that does not prevent the engagement element from engaging with the guide base when the mode selector is in the first state and a larger diameter that does prevent the engagement element for engaging with the guide base when the mode selector is in the second state.

13. The tibial cutting guide of claim 12 wherein the mode selector includes a transition portion with a diameter that changes between the smaller diameter and the larger diameter at a rate desirable to facilitate ergonomic operation of the mode selector.

14. The tibial cutting guide of claim 1, further comprising an engagement biasing element that presses the engagement element toward contact with the guidebase.

15. The tibial cutting guide of claim 1 wherein the mode selector includes a smaller diameter that does not prevent the engagement element from engaging with the cutting head when the mode selector is in the first state and a larger diameter that does prevent the engagement element for engaging with the cutting head when the mode selector is in the second state.

16. The tibial cutting guide of claim 15 wherein the mode selector includes a transition portion with a diameter that changes between the smaller diameter and the larger diameter at a rate desirable to facilitate ergonomic operation of the mode selector.

17. The tibial cutting guide of claim 1, further comprising an engagement biasing element that presses the engagement element toward contact with the cutting head.

18. The tibial cutting guide of claim 1 wherein the cutting head base includes one or more pin holes for receiving one or more fasteners by which the cutting head base may be coupled with a tibia.

19. The tibial cutting guide of claim 1 wherein the coupler of the removable mechanism includes a push portion that disengages a latch from a connection on the cutting head base, thereby allowing the removable mechanism to be separated from the cutting head base.

20. The tibial cutting guide of claim 1 wherein the blade guide is adapted to direct a blade through only a portion of the tibia aligning with a single condyle landing area of a knee joint to facilitate preparation for a unicondylar knee implant.

21. The tibial cutting guide of claim 1 wherein the microadjustment element moves the blade guide substantially parallel with the axis moved by the alignment mechanism relative to the guide base.

22. The tibial cutting guide of claim 1 wherein the blade guide comprises: a body;

an opening in the body sized and oriented to direct a blade by having a substantially close fit between a wider proportion side of the blade and the opening, wherein the opening has a greater longitudinal direction and a lesser height substantially perpendicular to the longitudinal direction; and a pin slot in the body having a width in substantially the same direction as the longitudinal direction of the opening and a height less than the width, wherein the pin slot is sized to have a substantially close fit between its height and a pin configured to be inserted through the pin slot and a looser fit between its width and the pin such that the pin is able to be moved along the width of the pin slot and pivot about an axis parallel to the height of the pin slot.

23. The tibial cutting guide of claim 22 wherein one or both edges of the pin slot at the extents of the width of the pin slot are angled substantially away from perpendicular to the longitudinal direction of the opening in the body.

24. The tibial cutting guide of claim 22 wherein both edges of the pin slot at the extents of the width of the pin slot are angled substantially away from perpendicular to the longitudinal direction of the opening in the body.

25. The tibial cutting guide of claim 22 wherein the pin slot is wider on the side of the blade guide configured to be positioned against a tibia than the pin slot is on the opposite side of the blade guide.

26. The tibial cutting guide of claim 22, further comprising a modular capture device comprising:

a pin opening sized to have a substantially close fit to the pin configured to be inserted through the pin slot; and a fin sized to engage in the opening in the body to provide orientation of the modular capture device relative to the body.

27. The tibial cutting guide of claim 26, further comprising an alignment slot in the modular capture device in which an alignment tool may be placed to orient the modular capture device relative to a patient's anatomy.

28. The tibial cutting guide of claim 1 wherein the removable mechanism includes one or more pin holes for receiving one or more fasteners by which the removable mechanism may be coupled with a tibia.

29. The tibial cutting guide of claim 1, further comprising a biasing element adapted to generate a biasing force to urge a distal end of the first arm toward a distal end of the second arm.

30. The tibial cutting guide of claim 29, further comprising a biasing force interface bracket configured to fit between the biasing element and the first arm and the second arm to apply biasing force from the biasing element to the first arm at a first point on the first arm away from the first pivot and to apply the biasing force from the biasing element to the second arm at a second point on the second arm away from the second pivot.

31. The tibial cutting guide of claim 29 wherein the biasing element includes two or more springs.

\* \* \* \* \*